United States Patent [19]
Schmeck et al.

[11] Patent Number: 5,932,587
[45] Date of Patent: Aug. 3, 1999

[54] HETEROCYCLIC-FUSED PYRIDINES

[75] Inventors: Carsten Schmeck, Wuppertal; Matthias Müller-Gliemann, Solingen; Gunter Schmidt; Arndt Brandes, both of Wuppertal, all of Germany; Rolf Angerbauer, Kobe, Japan; Michael Lögers, Wuppertal, Germany; Klaus-Dieter Bremm, Recklinghausen, Germany; Hilmar Bischoff, Wuppertal, Germany; Delf Schmidt, Wuppertal, Germany; Joachim Schuhmacher, Wuppertal, Germany

[73] Assignee: Bayer Aktiengesellschaft, Leverkusen, Germany

[21] Appl. No.: 08/883,673

[22] Filed: Jun. 27, 1997

[30] Foreign Application Priority Data

Jul. 8, 1996 [DE] Germany .................. 196 27 431

[51] Int. Cl.$^6$ .................. C07D 471/04; C07D 495/04; A61K 31/435
[52] U.S. Cl. .................. 514/278; 514/300; 514/301; 546/14; 546/18; 546/114; 546/116; 546/122; 546/123
[58] Field of Search .................. 546/14, 18, 114, 546/116, 122, 123; 514/300, 301, 302, 278

[56] References Cited

U.S. PATENT DOCUMENTS

| | | | |
|---|---|---|---|
| 4,814,346 | 3/1989 | Albert et al. | 514/454 |
| 5,006,530 | 4/1991 | Angerbauer et al. | 514/277 |
| 5,034,399 | 7/1991 | Hübsch et al. | 514/300 |
| 5,169,857 | 12/1992 | Angerbauer et al. | 514/344 |

FOREIGN PATENT DOCUMENTS

| | | |
|---|---|---|
| 325130 | 7/1989 | European Pat. Off. . |
| 391185 | 10/1990 | European Pat. Off. . |

OTHER PUBLICATIONS

Tetrahedron. vol. 40. No. 18. pp. 3431–3436, 1984, Ramesch. M. et al. Synthesis of 2–isopropylfuro (2.3–b) quinolines.

Monatsh. fur Chemie (1976), 107 (1), pp. 259–269. Shanmugan. P., et al. Furochinoline, 9. Mitt: Synthese von Furo [2,3–b] chinolinen.

*Primary Examiner*—Bernard Dentz
*Attorney, Agent, or Firm*—Sprung Kramer Schaefer & Briscoe

[57] ABSTRACT

The heterocyclic-fused pyridines are prepared by reaction of the corresponding heterocyclic-fused pyridine aldehydes with appropriately substituted Grignard or Wittig reagents. The heterocyclic-fused pyridines are suitable as active compounds in medicaments, in particular in medicaments for the treatment of dislipidaemia and arteriosclerosis.

10 Claims, No Drawings

HETEROCYCLIC-FUSED PYRIDINES

The present invention relates to heterocyclic-fused pyridines, processes for their preparation and their use in medicaments.

U.S. Pat. No. 5,169,857 discloses 7-(polysubstituted pyridyl)-6-heptenoates for the treatment of arteriosclerosis, lipoproteinaemia and hyperlipoproteinaemia. The preparation of 7-(4-aryl-3-pyridyl)-3,5-dihydroxy-6-heptenoates is additionally described in the publication EP 325 130 A2.

The present invention relates to heterocyclic-fused pyridines of the general formula (I)

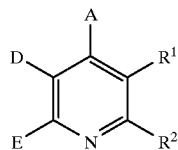

(I)

in which
A represents aryl having 6 to 10 carbon atoms, which is optionally substituted up to 5 times in an identical or different manner by halogen, hydroxyl, trifluoromethyl, nitro, trifluoromethoxy or by straight-chain or branched alkyl, acyl, hydroxyalkyl or alkoxy each having up to 7 carbon atoms, or by a group of the formula —$NR^3R^4$,
in which
$R^3$ and $R^4$ are identical or different and
denote hydrogen, phenyl or straight-chain or branched alkyl having up to 6 carbon atoms,
D represents a radical of the formula
$R^5$—X— or

in which
$R^5$ and $R^6$ independently of one another
denote cycloalkyl having 3 to 8 carbon atoms, or
aryl having 6 to 10 carbon atoms,
or a 5- to 7-membered aromatic, optionally benzo-fused heterocycle having up to 3 heteroatoms from the series consisting of S, N and/or O, each of which is optionally substituted up to 5 times in an identical or different manner by trifluoromethyl, trifluoromethoxy, nitro, halogen, hydroxyl, carboxyl, by straight-chain or branched alkyl, acyl, alkoxy or alkoxycarbonyl each having up to 6 carbon atoms or by phenyl, phenoxy or thiophenyl, which for their part can be substituted by halogen, trifluoromethyl or trifluoromethoxy, or the cycles are optionally substituted by a group of the formula —$NR^9R^{10}$,
in which
$R^9$ and $R^{10}$ are identical or different and have the meaning of $R^3$ and $R^4$ indicated above,
X denotes a straight-chain or branched alkylene or alkenylene chain each having up to 8 carbon atoms, each of which is optionally substituted up to 2 times by hydroxyl,
$R^7$ denotes hydrogen or halogen and
$R^8$ denotes hydrogen, halogen, azido, trifluoromethyl. hydroxyl, trifluoromethoxy, straight-chain or branched alkoxy having up to 5 carbon atoms or a radical of the formula —$NR^{11}R^{12}$,
in which
$R^{11}$ and $R^{12}$ are identical or different and have the meaning of $R^3$ and $R^4$ indicated above, or
$R^7$ and $R^8$, together with the C atom, form a carbonyl group,
E represents cycloalkyl having 3 to 8 carbon atoms, or represents straight-chain or branched alkyl having up to 8 carbon atoms, which is optionally substituted by cycloalkyl having 3 to 8 carbon atoms or by hydroxyl,
$R^1$ and $R^2$ together formn an alkylene chain having up to 6 carbon atoms, which is interrupted by an oxygen or sulphur atom or by the group —$SO_2$— or —$NR^{13}$,
where
$R^{13}$ denotes hydrogen or straight-chain or branched alkyl or acyl each having up to 6 carbon atoms, or
denotes benzyl or phenyl, each of which is optionally substituted up to 2 times in an identical or different manner by halogen, hydroxyl, nitro, trifluoromethyl or straight-chain or branched alkyl or acyl each having up to 6 carbon atoms,
and where the heterocyclic ring thus formed, which can also be benzo-fused and can contain a double bond, must always be substituted by a carbonyl group or a radical of the formula

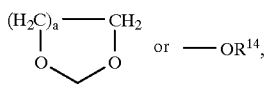 or —$OR^{14}$, in which
a denotes a number 1, 2 or 3 and
$R^{14}$ denotes hydrogen or straight-chain or branched alkyl, hydroxy-substituted alkyl, acyl or alkoxycarbonyl each having up to 6 carbon atoms or a radical of the formula —$SiR^{15}R^{16}R^{17}$,
in which
$R^{15}$, $R^{16}$ and $R^{17}$ are identical or different and denote phenyl, straight-chain or branched alkylene having up to 6 carbon atoms,
and the heterocyclic and/or benzo-fused ring ($R^1/R^2$) is optionally substituted up to 5 times in an identical or different manner, optionally also geminally, by straight-chain or branched alkoxy or alkoxycarbonyl each having up to 6 carbon atoms, trifluoromethyl, halogen, hydroxyl, carbonyl or phenyl which, for its part, can be substituted by halogen, trifluoromethyl, nitro, hydroxyl or by straight-chain or branched alkyl, alkoxy or alkoxycarbonyl each having up to 6 carbon atoms,
and/or is optionally substituted up to 6 times, optionally also geminally, in an identical or different manner by cycloalkyl or cycloalkyloxy each having 3 to 8 carbon atoms or by straight-chain or branched alkyl having up to 6 carbon atoms, which for its part can be substituted by hydroxyl, trifluoromethyl, phenyl or by straight-chain or branched alkoxy having up to 5 carbon atoms,
and/or is optionally substituted by a spiro-linked radical of the formula

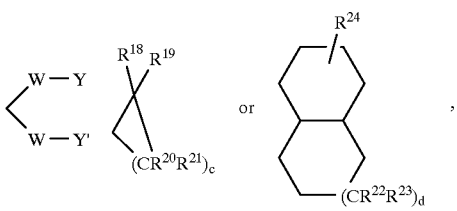

in which

W denotes either an oxygen or a sulphur atom,

Y and Y' together form a 2- to 6-membered straight-chain or branched alkylene chain, c denotes a number 1, 2, 3, 4, 5, 6 or 7, d denotes a number 1 or 2, $R^{18}$, $R^{19}$, $R^{20}$, $R^{21}$, $R^{22}$, $R^{23}$ and $R^{24}$ are identical or different and denote hydrogen, trifluoromethyl, phenyl, halogen or straight-chain or branched alkyl or alkoxy each having up to 6 carbon atoms or $R^{18}$ and $R^{19}$ or $R^{20}$ and $R^{21}$ in each case together form a straight-chain or branched alkylene chain having up to 6 carbon atoms or $R^{18}$ and $R^{19}$ or $R^{20}$ and $R^{21}$ in each case together form a radical of the formula

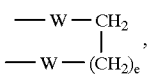

in which

W has the meaning indicated above, e denotes a number 1, 2, 3, 4, 5, 6 or 7, and their salts and N-oxides.

The heterocyclic-fused pyridines according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, methanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, if appropriate benzo-fused, in the context of the invention in general represents a saturated or unsaturated 5- to 7-membered, preferably 5- to 6-membered, heterocycle, which can contain up to 3 heteroatoms from the series consisting of S, N and/or O. Examples which may be mentioned are: indolyl, isoquinolyl, quinolyl, benzo[b]thiophenyl, benzothiazolyl, benzo[b]furanyl, pyridyl, thienyl, furyl, pyrrolyl, thiazolyl, oxazolyl, imidazolyl, morpholinyl or piperidyl. Quinolyl, indolyl, pyridyl and benzothiazolyl are preferred.

Preferred compounds of the general formula (I) are those in which

A represents naphthyl or phenyl, each of which is optionally substituted up to 3 times in an identical or different manner by fluorine, chlorine, bromine, hydroxyl, trifluoromethyl, trifluoromethoxy, nitro or by straight-chain or branched alkyl, acyl or alkoxy each having up to 6 carbon atoms or by a group of the formula —$NR^3R^4$, in which $R^3$ and $R^4$ are identical or different and denote hydrogen, phenyl or straight-chain or branched alkyl having up to 4 carbon atoms, D represents a radical of the formnula $R^5$—X— or

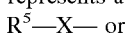
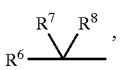

in which $R^5$ and $R^6$ independently of one another denote cyclopropyl, cyclopentyl or cyclohexyl, or denote naphthyl, phenyl, pyridyl, quinolyl, indolyl, benzothiazolyl or tetrahydronaphthalenyl, each of which is optionally substituted up to 3 times in an identical or different manner by trifluoromethyl, trifluoromethoxy, fluorine, chlorine, bromine, hydroxyl, carboxyl, by straight-chain or branched alkyl, acyl, alkoxy or alkoxycarbonyl each having up to 5 carbon atoms or by phenyl, phenoxy or thiophenyl, which for their part can be substituted by fluorine, chlorine, bromine, trifluoromethyl or trifluoromethoxy, or the cycles are optionally substituted by a group of the formula —$NR^9R^{10}$, in which $R^9$ and $R^{10}$ are identical or different and have the meaning of $R^3$ and $R^4$ indicated above, X denotes a straight-chain or branched alkylene or alkenylene chain each having up to 6 carbon atoms, each of which is optionally substituted up to 2 times by hydroxyl, $R^7$ denotes hydrogen, fluorine or chlorine and $R^8$ denotes hydrogen, fluorine, chlorine, bromine, azido, trifluoromethyl, hydroxyl, trifluoromethoxy, straight-chain or branched alkoxy having up to 4 carbon atoms or a radical of the formula —$NR^{11}R^{12}$, in which $R^{11}$ and $R^{12}$ are identical or different and have the meaning of $R^3$ and $R^4$ indicated above, or $R^7$ and $R^8$ together with the C atom form a carbonyl group, E represents cyclopropyl, cyclobutyl, cyclopentyl, cyclohexyl or cycloheptyl, or represents straight-chain or branched alkyl having up to 6 carbon atoms, which is optionally substituted by cyclopropyl, cyclobutyl, cyclopentyl, cyclohexyl, cycloheptyl or by hydroxyl, $R^1$ and $R^2$ together form an alkylene chain having up to 5 carbon atoms, which is interrupted by an oxygen or sulphur atom or by the group —SO$_2$— or —NR$^{13}$,
where
$R^{13}$ denotes hydrogen or straight-chain or branched alkyl or acyl each having up to 5 carbon atoms, or
denotes benzyl or phenyl, each of which is optionally substituted up to 2 times in an identical or different manner by fluorine, chlorine, bromine, hydroxyl, nitro, trifluoromethyl or straight-chain or branched alkyl or acyl each having up to 4 carbon atoms,
and where the heterocyclic ring thus formed, which can also be benzo-fused and can contain a double bond, must always be substituted by a carbonyl group or by a radical of the formula

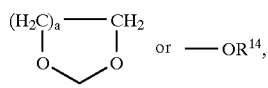

in which
a denotes a number 1, 2 or 3 and
$R^{14}$ denotes hydrogen or straight-chain or branched alkyl, hydroxy-substituted alkyl or alkoxycarbonyl each having up to 5 carbon atoms or a radical of the formula —SiR$^{15}$R$^{16}$R$^{17}$,
in which
$R^{15}$, $R^{16}$ and $R^{17}$ are identical or different and denote phenyl, straight-chain or branched alkyl having up to 5 carbon atoms,
and the heterocyclic and/or benzo-fused ring ($R^1/R^2$) is optionally substituted up to 3 times in an identical or different manner, optionally also geminally, by straight-chain or branched alkoxy or alkoxycarbonyl each having up to 4 carbon atoms, hydroxyl, carboxyl or phenyl, which for its parts can be substituted by fluorine, chlorine, bromine, trifluoromethyl or by straight-chain or branched alkyl or alkoxy each having up to 4 carbon atoms,
and/or is optionally substituted up to 4 times, optionally also geminally, in an identical or different manner by cyclopropyl, cyclopropyloxy, cyclopentyl, cyclopentyloxy, cyclohexyl, cyclohexyloxy or by straight-chain or branched alkyl having up to 4 carbon atoms, which for its part can be substituted by hydroxyl, trifluoromethyl, phenyl or by straight-chain or branched alkoxy having up to 3 carbon atoms
and/or is optionally substituted by a spiro-linked radical of the formula

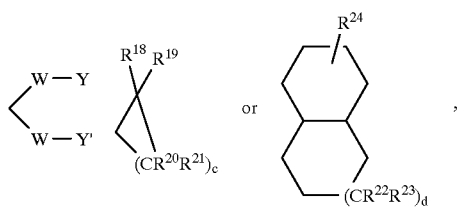

in which
W denotes either an oxygen or a sulphur atom,
Y and Y' together form a 2- to 5-membered, straight-chain or branched alkylene chain,
c denotes a number 1, 2, 3, 4, 5 or 6,
d denotes a number 1 or 2,
$R^{18}$, $R^{19}$, $R^{20}$, $R^{21}$, $R^{22}$, $R^{23}$ and $R^{24}$ are identical or different and denote hydrogen, trifluoromethyl, phenyl, fluorine, chlorine, bromine or straight-chain or branched alkyl or alkoxy each having up to 5 carbon atoms or
$R^{18}$ and $R^{19}$ or $R^{20}$ and $R^{21}$ in each case together form a straight-chain or branched alkylene chain having up to 5 carbon atoms or
$R^{18}$ and $R^{19}$ or $R^{20}$ and $R^{21}$ in each case together form a radical of the formula

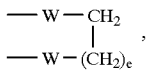

in which
W has the meaning indicated above,
e denotes a number 1, 2, 3, 4, 5 or 6,
and their salts and N-oxides.

Particularly preferred compounds of the general formula (I) according to the invention are those
in which
A represents phenyl which is optionally substituted by fluorine, chlorine, bromine, hydroxyl, trifluoromethyl, trifluoromethoxy, nitro or by straight-chain or branched alkyl or alkoxy each having up to 3 carbon atoms,
D represents a radical of the formula
$R^5$—X— or

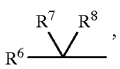

in which
$R^5$ and $R^6$ independently of one another
denote cyclopropyl, naphthyl, phenyl, pyridyl, quinolyl, indolyl, benzothiazolyl or tetrahydronaphthalenyl, each of which is optionally substituted up to 2 times in an identical or different manner by trifluoromethyl, trifluoromethoxy, fluorine, chlorine, bromine, hydroxyl, carboxyl, amino, by straight-chain or branched alkyl, acyl, alkoxy or alkoxycarbonyl each having up to 4 carbon atoms or by phenyl, phenoxy or thiophenyl, which for their part can be substituted by fluorine, chlorine, bromine, trifluoromethyl or trifluoromethoxy,
X denotes a straight-chain or branched alkylene or alkenylene chain having up to 4 carbon atoms, each of which is optionally substituted by hydroxyl,
$R^7$ denotes hydrogen or fluorine and
$R^8$ denotes hydrogen, fluorine, chlorine, bromine, azido, trifluoromethyl, hydroxyl, amino, trifluoromethoxy or methoxy, or
$R^7$ and $R^8$, together with the carbon atom, form a carbonyl group,
E represents cyclopropyl, cyclobutyl, cyclopentyl, cyclohexyl or cycloheptyl, or represents straight-chain or branched alkyl having up to 5 carbon atoms, which is optionally substituted by cyclopentyl or cyclohexyl,
$R^1$ and $R^2$ together form an alkylene chain having up to 4 carbon atoms, which is interrupted by an oxygen or sulphur atom or by the group —SO$_2$— or —NR$^{13}$,
where
$R^{13}$ denotes hydrogen, phenyl or straight-chain or branched acyl or alkyl each having up to 4 carbon atoms, or denotes benzyl or phenyl, each of which is optionally substituted up to 2 times in an identical or different manner by fluorine, chlorine, bromine, hydroxyl, nitro, trifluoromethyl or straight-chain or branched alkyl or acyl each having up to 3 carbon atoms, and where the heterocyclic ring thus formed, which can also be benzo-fused and which can contain a double bond, must always be substituted by a carbonyl group or by a radical of the formula

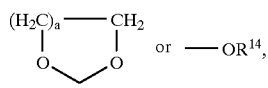

in which a denotes a number 1, 2 or 3 and $R^{14}$ denotes hydrogen or straight-chain or branched alkyl or hydroxy-substituted alkyl or alkoxycarbonyl each having up to 4 carbon atoms or a radical of the formula $-SiR^{15}R^{16}R^{17}$, in which $R^{15}$, $R^{16}$ and $R^{17}$ are identical or different and denote phenyl, straight-chain or branched alkyl having up to 4 carbon atoms, and the heterocyclic and/or benzo-fused ring ($R^1/R^2$) is optionally substituted up to 3 times in an identical or different manner, optionally also geminally, by straight-chain or branched alkoxy or alkoxycarbonyl each having up to 3 carbon atoms, hydroxyl, carboxyl or phenyl which, for its part, can be substituted by fluorine, chlorine, bromine, trifluoromethyl or by straight-chain or branched alkyl having up to 3 carbon atoms, and/or is optionally substituted up to 3 times, optionally also geminally, in an identical or different manner by cyclopropyl, cyclopropyloxy, cyclopentyl, cyclopentyloxy, cyclohexyl or by straight-chain or branched alkyl having up to 3 carbon atoms, which for its part can be substituted by hydroxyl, trifluoromethyl, phenyl or methoxy and/or is optionally substituted by a spiro-linked radical of the formula

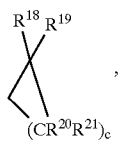

in which c denotes a number 1, 2, 3, 4 or 5, $R^{18}$, $R^{19}$, $R^{20}$ and $R^{21}$ are identical or different and denote hydrogen, trifluoromethyl, phenyl, fluorine, chlorine, bromine or straight-chain or branched alkyl or alkoxy each having up to 4 carbon atoms or $R^{18}$ and $R^{19}$ or $R^{20}$ and $R^{21}$ in each case together form a straight-chain or branched alkyl chain having up to 4 carbon atoms or $R^{18}$ and $R^{19}$ or $R^{20}$ and $R^{21}$ in each case together form a radical of the formula

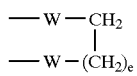

in which

W denotes either an oxygen or sulphur atom and e denotes a number 1, 2, 3, 4 or 5, and their salts and N-oxides.

Very particularly preferred compounds of the general formula (I) are those in which A represents phenyl which is optionally substituted by fluorine and E represents cyclopentyl or isopropyl, and their salts and N-oxides.

A process for the preparation of the compounds of the general formula (I) according to the invention has additionally been found, characterized in that in the compounds of the general formula (II)

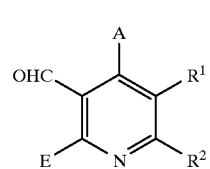

(II)

in which

A, E, $R^1$ and $R^2$ have the meaning indicated above, first, with organometallic reagents, the substituent D is introduced in inert solvents according to a Grignard or Wittig reaction, and if appropriate the substituents mentioned under A, E and/or $R^1$ and $R^2$ are varied or introduced according to customary methods.

The process according to the invention can be illustrated by way of example by the following reaction scheme:

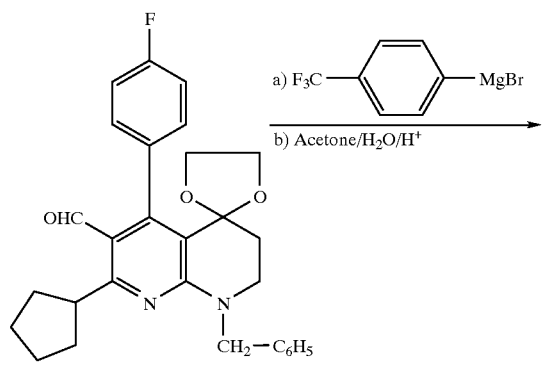

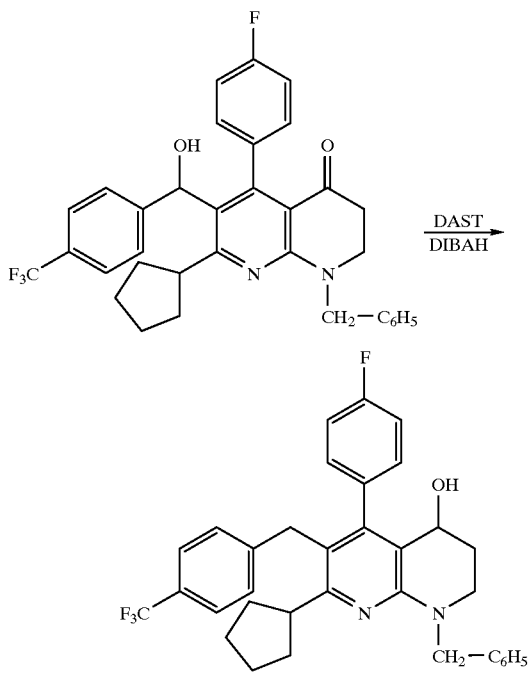

Suitable solvents are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane and tetrahydrofuran are preferred.

Possible bases for the individual steps are the customary strongly basic compounds. These preferably include organolithium compounds such as, for example, lithium bis(triethylbutyl)amide, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride or alkoxides such as, for example, potassium tert-butoxide. n-Butyllithium, sodium hydride or potassium tert-butoxide is particularly preferably employed.

Suitable organometallic reagents are, for example, systems such as Mg/bromobenzotrifluoride and p-trifluoromethylphenyllithium. The system Mg/bromobenzotrifluoride is preferred.

Suitable Wittig reagents are the customary reagents. 3-Tri-fluoromethylbenzyltriphenylphosphonium bromide is preferred.

In general, suitable bases are one of the abovementioned bases, preferably Li bis-(triethylbutyl)amide or n-butyllithium.

The base is employed in an amount from 0.1 mol to 5 mol, preferably from 0.5 mol to 2 mol, in each case relative to 1 mol of the starting compound.

The reaction with Wittig reagents is in general carried out in a temperature range from 0° C. to 150° C., preferably at 25° C. to 40° C.

The Wittig reactions are in general carried out at normal pressure. However, it is also possible to carry out the process at reduced pressure or at elevated pressure (e.g. in the range from 0.5 to 5 bar).

The reductions are in general carried out using reducing agents, preferably using those which are suitable for the reduction of ketones to hydroxyl compounds. Particularly suitable in this context is reduction with metal hydrides or complex metal hydrides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkylborohydride or lithium aluminium hydride or diisobutylaluminum hydride (DIBAH). The reduction is very particularly preferably carried out using sodium borohydride or DIBAH, in the presence of triethylborane.

The reducing agent is in general employed in an amount from 4 mol to 10 mol, preferably from 4 mol to 5 mol, relative to 1 mol of the compounds to be reduced.

The reduction in general proceeds in a temperature range from −78° C. to +50° C., preferably from −78° C. to 0° C., particularly preferably at −78° C., in each case depending on the choice of the reducing agent and solvent.

The reduction in general proceeds at normal pressure, but it is also possible to work at elevated or reduced pressure.

The hydrogenation is carried out according to customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range from −20° C. to +100° C., preferably from 0° C. to +50° C., at normal pressure or elevated pressure.

Derivatizations which may be mentioned by way of example are the following types of reactions: oxidations, reductions, hydrogenations, halogenation, Wittig/Grignard reactions and amidations/sulphoamidations.

Possible bases for the individual steps are the customary strongly basic compounds. These preferably include organolithium compounds such as, for example, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. n-Butyllithium or sodium hydride is particularly preferably employed.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydroxide or potassium hydroxide is particularly preferably employed.

Suitable solvents for the individual reaction steps are also alcohols such as methanol, ethanol, propanol, butanol or tert-butanol. tert-Butanol is preferred.

It may be necessary to carry out some reaction steps under a protective gas atmosphere.

The halogenations are in general carried out in one of the abovementioned chlorinated hydrocarbons, methylene chloride being preferred.

Suitable halogenating agents are, for example, diethylaminosulphur trifluoride (DAST) or $SOCl_2$.

The halogenation in general proceeds in a temperature range from −78° C. to +50° C., preferably from −78° C. to 0° C., particularly preferably at −78° C., in each case depending on the choice of the halogenating agent and solvent.

The halogenation in general proceeds at normal pressure, but it is also possible to work at elevated or reduced pressure.

The compounds of the general formula (II) are new and can be prepared by a process in which

[A] compounds of the general formula (III)

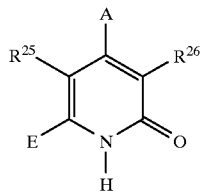

(III)

in which

A and E have the meaning indicated above, and $R^{25}$ and $R^{26}$ are identical or different and denote $C_1$–$C_4$-alkoxycarbonyl, are first converted with phosphorus oxychloride into the compounds of the general formula (IV)

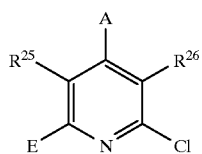

(IV)

in which

A, E, $R^{25}$ and $R^{26}$ have the meaning indicated above, and, depending on the meaning of $R^1$ and $R^2$ indicated above, these are then converted by a nucleophilic substitution in inert solvents, if appropriate in the presence of a base into the compounds of the general formula (V)

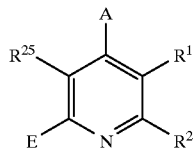

(V)

in which

A, E, $R^1$, $R^2$ and $R^{25}$ have the meaning indicated above, in inert solvents and if appropriate in the presence of a base, or in that

[B] compounds of general formula (VI)

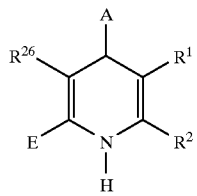

(VI)

in which

A, E, $R^1$ and $R^2$ have the meaning indicated above and $R^{26}$ has the meaning indicated above, are first converted by an oxidation into the compounds of the general formula (Va)

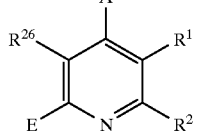

(Va)

in which

A, E, $R^1$, $R^2$ and $R^{26}$ have the meaning indicated above, and are then reacted further as described under [A], and, if appropriate, in all stages derivatizations such as, for example, an alkylation or halogenation or eliminations, or introductions of protective groups are carried out according to customary methods, and in a last step the alkoxycarbonyl function ($R^{26}$) is reacted according to customary methods to give the aldehyde.

The process according to the invention can be illustrated by way of example by the following reaction scheme:

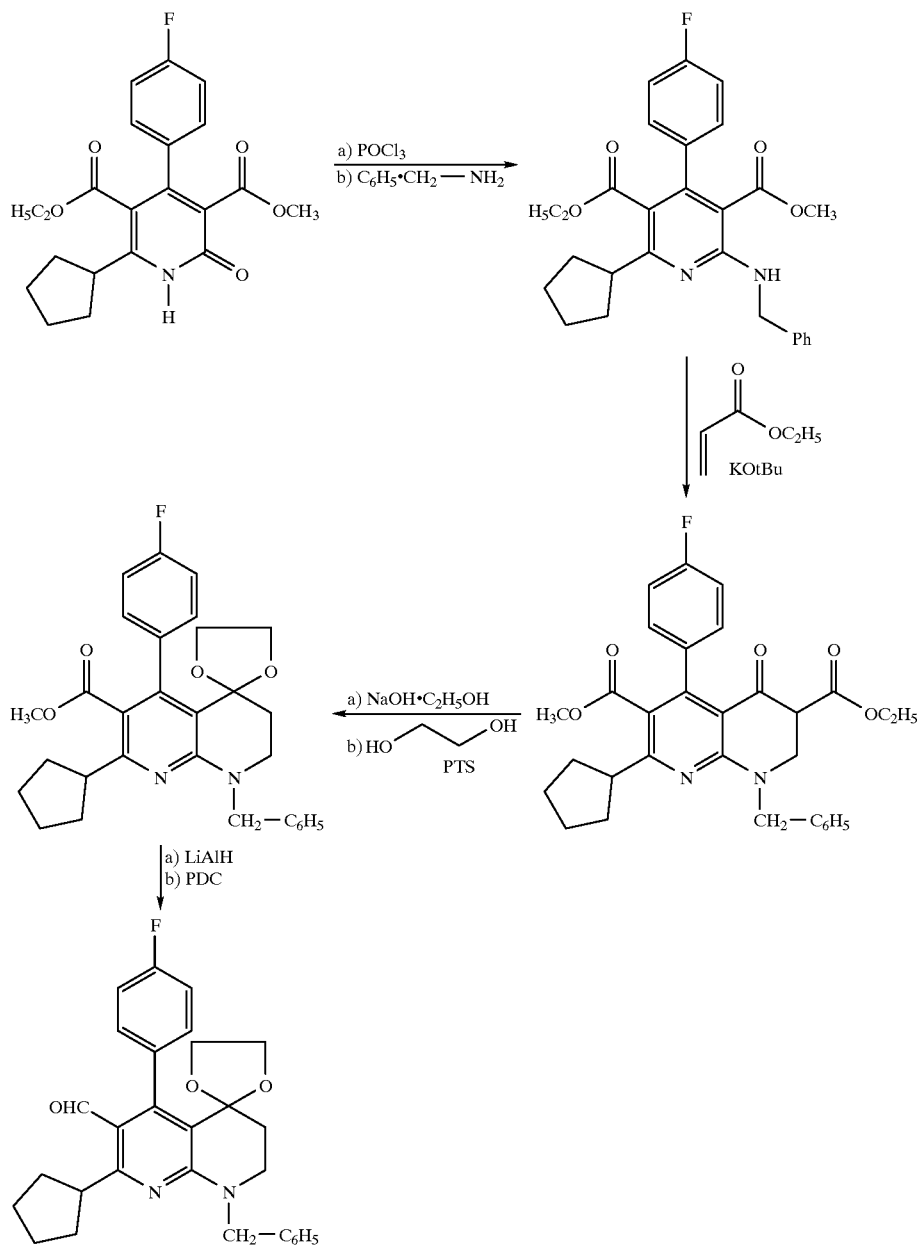

Suitable solvents for the individual steps are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile. acetone or nitromethane or alcohols, such as, for example, methanol, ethanol or propanol. It is also possible to use mixtures of the solvents mentioned. Dichloromethane. acetonitrile. ethanol and tetrahydrofuran are preferred.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate, sodium methoxide or potassium tert-butoxide or sodium hydrogen carbonate. Sodium hydroxide, potassium hydroxide or potassium tert-butoxide is particularly preferably employed.

The base is in general employed in an amount from 0.5 mol to 5 mol, preferably from 1 mol to 2.5 mol, in each case relative to 1 mol of the compounds of the general formulae (V) and (Va).

The reaction is in general carried out at normal pressure. However, it is also possible to carry out the process at reduced pressure or at elevated pressure (e.g. in a range from 0.5 to 5 bar).

The compounds of the general formula (III) are known in some cases or are new and can then be prepared, however, from the corresponding 2-oxo- 1,2,3,4-tetrahydropyridines by an oxidation.

Suitable solvents for the oxidation are ethers such as diethyl ether, dioxane, tetrahydrofuran, glycol dimethyl ether, or hydrocarbons such as benzene, toluene, xylene, hexane, cyclohexane or petroleum fractions, or halogeno-hydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone, nitromethane or water. It is also possible to use mixtures of the solvents mentioned.

Acetonitrile and water are preferred.

Suitable oxidizing agents are, for example, cerium(IV) ammonium nitrate, 2,3-dichloro-5,6-dicyano-benzoquinone, pyridinium chlorochromate (PCC), osmium tetroxide and manganese dioxide. Cerium(IV) ammonium nitrate is preferred.

The oxidizing agent is employed in an amount from 1 mol to 10 mol, preferably from 2 mol to 5 mol, relative to 1 mol of the compounds of the general formula (IV).

The oxidation in general proceeds in a temperature range from −50° C. to +100° C., preferably from 0° C. to room temperature.

The oxidation in general proceeds at normal pressure. However, it is also possible to carry out the oxidation at elevated or reduced pressure.

The compounds of the general formula (IV) are for the most part new and can be prepared as described above.

The compounds of the general formulae (V) and (Va) are for the most part new and can be prepared as described above.

The compounds of the general formula (VI) are for the most part new and can be prepared as described above, by a process in which aldehydes of the general formula (VII)

A—CHO         (VII)

in which
A has the meaning indicated above,
are reacted with compounds of the general formula (VIII)

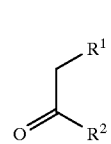

(VIII)

in which
$R^1$ and $R^2$ have the meaning indicated above,
and the compound of the general formula (IX)

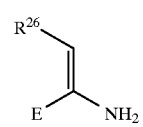

(IX)

in which
E and $R^{26}$ have the meaning indicated above,
in one of the abovementioned solvents, preferably ethanol, at reflux temperature and normal pressure.

The compounds of the general formula (VII), (VIII) and (IX) are known per se or can be prepared by customary methods.

The compounds of the general formula (I) according to the invention have an unforeseeable spectrum of pharmacological action.

The compounds of the general formula (I) according to the invention have useful pharmacological properties which are superior in comparison with those of the prior art, in particular they are highly effective inhibitors of the cholesterol ester transfer protein (CETP) and stimulate reverse cholesterol transport. The active compounds according to the invention bring about a lowering of the LDL cholesterol level in the blood with a simultaneous increase in the HDL cholesterol level. They can therefore be used for the treatment and prevention of hyperlipoproteinaemia, dyslipidaemias. hypertriglyceridaemias, hyperlipidaemias or arteriosclerosis.

The pharmacological actions of the substances according to the invention were determined in the following test:

CETP Inhibition Testing

Obtainment of CETP

CETP is obtained from human plasma in partially purified form by differential centrifugation and column chromatography and used for the test. To this end, human plasma is adjusted to a density of 1.21 g per ml using NaBr and centrifuged at 4° C. for 18 h at 50,000 rpm. The bottom fraction (d>1.21 g/ml) is applied to a Sephadex®phenyl-sepharose 4B (Pharmacia) column, washed with 0.15 M NaCl/0.001 M tris HCl pH 7.4 and then eluted with distilled water. The CETP-active fractions are pooled, dialysed against 50 mM Na acetate pH 4.5 and applied to a CM-Sepharose® (Pharmacia) column. The column is then eluted using a linear gradient (0–1 M NaCl). The pooled CETP fractions are dialysed against 10 mM tris HCl pH 7.4 and then further purified by chromatography on a Mono Q® column (Pharmacia).

Obtainment of radiolabelled HDL 50 ml of fresh human EDTA plasma are adjusted to a density of 1.12 using NaBr and centrifuged at 50,000 rpm for 18 h at 4° C. in a Ty 65 rotor. The upper phase is used to obtain cold LDL. The lower phase is dialysed against 3×4 l of PDB buffer (10 mM tris/HCl pH 7.4, 0.15 mM NaCl, 1 mM EDTA, 0.02% $NaN_3$). 20 µl of $^3$H-cholesterol (Dupont NET-725; 1 µC/µl dissolved in ethanol) are then added per 10 ml of retentate volume and the mixture is incubated under $N_2$ at 37° C. for 72 h.

The mixture is then adjusted to the density 1.21 using NaBr and centrifuged at 20° C. for 18 h at 50,000 rpm in the Ty 65 rotor. The upper phase is recovered and the lipoprotein fractions are purified by gradient centrifugation. To this end, the isolated, labelled lipoprotein fraction is adjusted to a density of 1.26 using NaBr. Each 4 ml of this solution are covered with a layer of 4 ml of a solution of density 1.21 and 4.5 ml of a solution of 1.063 (density solutions from PDB buffer and NaBr) in centrifuge tubes (SW 40 rotor) and then centrifuged in the SW 40 rotor for 24 h at 38,000 rpm and 20° C. The intermediate layer lying between the densities 1.063 and 1.21 and containing the labelled HDL is dialysed at 4° C. against 3×100 volumes of PDB buffer. The retentate contains radiolabelled $^3$H-CE-HDL which, adjusted to about 5×10$^6$ cpm per ml, is used for the test.

CETP Test

To test the CETP activity, the transfer of $^3$H-cholesterol ester from human HD lipoproteins to biotinylated LD lipoproteins is measured. The reaction is ended by addition of streptavidin-SPA®beads (Amersham) and the transferred radioactivity is determined directly in a liquid scintillation counter.

In the test mixture, 10 μl of HDL-$^3$H-cholesterol ester (~50,000 cpm) are incubated at 37° C. for 18 h with 10 μl of biotin-LDL (Amersham) in 50 mM Hepes/0.15 M NaCl/0.1% bovine serum albumin/0.05% NaN$_3$ pH 7.4 with 10 μl of CETP (1 mg/ml) and 3 μl of solution of the substance to be tested (dissolved in 10% DMSO/1% RSA). 200 μl of the SPA-streptavidin bead solution (TRKQ 7005) are then added, the mixture is incubated further for 1 h with shaking and then measured in the scintillation counter. As controls, corresponding incubations with 10 μl of buffer, 10 μl of CETP at 4° C. and 10 μl of CETP at 37° C. are used.

The activity transferred into the control mixtures with CETP at 37° C. is rated as 100% transfer. The substance concentration at which this transfer is reduced by half is indicated as the $IC_{50}$ value.

In Table A which follows, the $IC_{50}$ values (mol/l) are indicated for CETP inhibitors:

TABLE A

| Example No. | $IC_{50}$ value (mol/l) |
|---|---|
| 12 | $2 \times 10^{-7}$ |
| 14 | $6 \times 10^{-6}$ |
| 16 | $8.5 \times 10^{-7}$ |

Ex vivo activity of the compounds according to the invention

Syrian golden hamsters from in-house breeding are anaesthetized after fasting for 24 hours (0.8 mg/kg of atropine, 0.8 mg/kg of Ketavet® s.c., 30' later 50 mg/kg of Nembutal i.p.). The jugular vein is then exposed and cannulated. The test substance is dissolved in a suitable solvent (as a rule Adalat placebo solution: 60 g of glycerol, 100 ml of H$_2$O, PEG-400 to 1000 ml) and administered to the animals via a PE catheter inserted in the jugular vein. The control animals receive the same volume of solvent without test substance. The vein is then tied off and the wound is closed.

The administration of the test substances can also be carried out p.o., by orally administering the substances dissolved in DMSO and suspended in 0.5% Tylose by means of a stomach tube. The control animals receive identical volumes of solvent without test substance.

After various times—up to 24 hours after administration—blood (about 250 μl) is taken from the animals by puncture of the retro-orbital venous plexus. Clotting is ended by incubation at 4° C. overnight, then centrifugation is carried out at 6000×g for 10 minutes. In the serum thus obtained, CETP activity is determined by the modified CETP test. As for the CETP test described above, the transfer of $^3$H-cholesterol ester from HD lipoproteins to biotinylated LD lipoproteins is measured.

The reaction is ended by addition of Streptavidin-SPA®beads (Amersham) and the transferred radioactivity is determined directly in the liquid scintillation counter.

The test mixture is carried out as described under "CETP test". For the testing of the serum, only 10 μl of CETP are replaced by 10 μl of the corresponding serum samples. As controls, corresponding incubations with sera of untreated animals are used.

The activity transferred in the control mixtures with control sera is rated as 100% transfer. The substance concentration at which this transfer is reduced to a half is indicated as the $ED_{50}$ value.

TABLE B

| | $ED_{50}$ values for ex vivo activity | |
|---|---|---|
| Example No. | $ED_{50}$ | % Inhibition at 10 mg/kg |
| 12 | <10 mg/kg | 49.5% |
| 20 | >10 mg/kg | 50.4% |
| 21 | >10 mg/kg | 34.4% |

In vivo activity of the compounds according to the invention

In experiments to determine the oral action on lipoproteins and triglycerides, test substance dissolved in DMSO and 0.5% Tylose suspended by means of a stomach tube are administered orally to Syrian golden hamsters from in-house breeding. To determine the CETP activity, blood (about 250 μl) is taken by retro-orbital puncture before the start of the experiment. The test substances are then administered orally by means of a stomach tube. The control animals receive identical volumes of solvent without test substance. The feed is then withdrawn from the animals and blood is taken at various times—up to 24 hours after substance administration—by puncture of the retro-orbital venous plexus.

Clotting is ended by incubation at 4° C. overnight, then centrifugation at 6000×g is carried out for 10 minutes. In the serum thus obtained, the content of cholesterol and triglycerides is determined with the aid of modified commercially available enzyme tests (cholesterol enzymatic 14366 Merck, triglycerides 14364 Merck). Serum is suitably diluted using physiological saline solution.

100 μl of serum dilution are mixed with 100 μl of test substance in 96-hole plates and incubated at room temperature for 10 minutes. The optical density is then determined at a wavelength of 492 nm using an automatic plate-reading apparatus. The triglyceride or cholesterol concentration contained in the samples is determined with the aid of a standard curve measured in parallel. The determination of the content of HDL cholesterol is carried out according to the manufacturer's instructions after precipitation of the ApoB-containing lipoproteins by means of a reagent mixture (Sigma 352-4 HDL cholesterol reagent).

TABLE C

| | HDL rise in in vivo experiments | |
|---|---|---|
| Example No. | Dose (mglkg) | % HDL rise |
| 12 | 2 × 3 | 12.37 |
| 20 | 2 × 3 | 9.21 |

In vivo activity in transgenic hCETP mice

Transgenic mice from in-house breeding (Dinchuck, Hart, Gonzalez Karmann Schmidt, Wirak; BBA (1995), 1295, 301) were administered the substances to be tested in the feed. Before the start of the experiment, blood was taken retro-orbitally from the mice in order to determine cholesterol and triglycerides in the serum. The serum was obtained as described above for hamsters by incubation at 4° C. overnight and subsequent centrifugation at 6000×g. After one week, blood was again taken from the mice in order to determine lipoproteins and triglycerides. The change in the parameters measured is expressed as a percentage change compared with the starting value.

TABLE D

| Example No. | HDL | LDL | Triglycerides |
|---|---|---|---|
| 20 (80 ppm) | +14.5% | +6.7% | −24.5% |

The invention additionally relates to the combination of heterocyclic-fused pyridines of the general formula (I) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formnula (I) according to the invention is preferred.

The compounds according to the invention can furthermore be used in combination with cholesterol-lowering vastatins or ApoB-lowering principles in order to treat dyslipidaemias, combined hyperlipidaemias, hypercholesterolaemias or hypertriglyceridaemias.

The combinations mentioned can also be employed for the primary or secondary prevention of coronary heart disease (e.g. myocardial infarct).

Vastatins in the context of the invention are, for example, lovastatin, simvastatin pravastatin, fluvastatin, atorvastatin and cerivastatin. ApoB-lowering agents are, for example, MTP inhibitors. The combination of cerivastatin or ApoB inhibitors with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of approximately 0.5 to 90% by weight of the total mixture, i.e. in amounts which are adequate in order to achieve the dosage range indicated.

The formulations are prepared, for example, by extending the active compounds with solvents and/or excipients, if appropriate using emulsifiers and/or dispersants, it being possible, for example, when water is used as a diluent, optionally to use organic solvents as auxiliary solvents.

Administration is carried out intravenously, parenterally, perlingually or preferably orally in a customary manner.

In the case of parenteral administration, solutions of the active compound can be employed using suitable liquid excipient materials.

In general, it has proved advantageous in the case of intravenous administration to administer amounts of approximately 0.001 to 1 mg/kg, preferably of approximately 0.01 to 0.5 mg/kg of body weight to achieve effective results, and in the case of oral administration the dose is approximately 0.01 to 20 mg/kg, preferably 0.1 to 10 mg/kg of body weight.

In spite of this, if appropriate it may be necessary to deviate from the amounts mentioned, mainly depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

Abbreviations used:
DAST=dimethylaminosulphur trifluoride
PTS=para-toluenesulphonic acid
PDC=pyridinium dichromate
PE/EA=petroleum ether/ethyl acetate
THF=tetrahydrofuran
Tol/EA=toluene ethyl acetate

EXAMPLE I

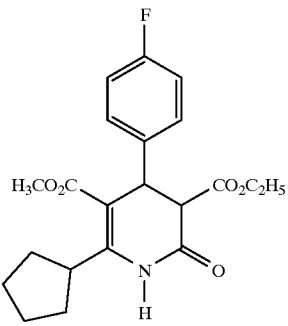

50 g (300 mmol) of methyl 3-amino-3-cyclopentyl-prop-2-ene carboxylate, 78.7 g (300 mmol) of diethyl 2-(4-fluorobenzylidene)-malonate, 1.1 g (20 mmol) of sodium methoxide and 6 ml of ethanol are heated at 140° C. for 80 hours with stirring. After cooling to room temperature, 500 ml of ethyl acetate are added and the solution is washed successively with 100 ml each of water and saturated sodium chloride solution. The organic phase is dried over sodium sulphate. After concentrating in vacuo, the residue is heated to boiling in 300 ml of cyclohexane with stirring and then slowly cooled to room temperature. The precipitated solid is dried to constant weight in vacuo.

Yield: 74.9 g (65% of theory); $R_f$=0.41 (PE/EA 4:1)

EXAMPLE II

3-Ethyl 5-methyl 6-cyclopentyl-4-(4-fluorophenyl)-2-oxo-1,2-dihydropyridine-3,5-dicarboxylate

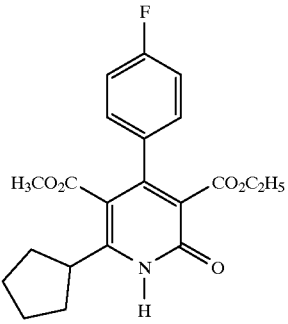

38 g (98 mmol) of the compound from Example I are dissolved in 300 ml of acetonitrile and treated with 120 g of cerium(IV) ammonium nitrate, dissolved in 300 ml of water, at room temperature in the course of 1 hour. The mixture is then stirred at room temperature for 3 hours, a white solid precipitating. To complete the crystallization, the mixture is allowed to stand at 5° C. for 16 hours. The solid is filtered off with suction and washed in small portions with 100 ml of water. The white solid is dried in vacuo for 2 days.

Yield: 31.6 g (83% of theory); $R_f$=0.28 (PE/EA 4:1)

EXAMPLE III

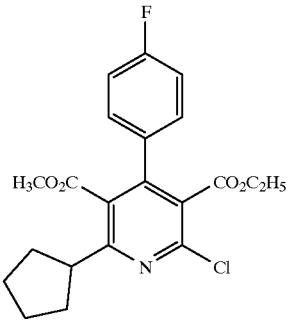

30.5 g (79 mmol) of the compound from Example II are stirred at 110° C. for 18 hours in 80 ml of phosphorus oxychloride. After cooling to room temperature, the phosphorus oxychloride is removed in vacuo. The residue is neutralized with saturated sodium hydrogen carbonate solution with ice-cooling and extracted twice with 150 ml of dichloromethane each time. The combined organic phases are dried over sodium sulphate and filtered through 250 g of silica gel (230–400 mesh). The residue is washed twice more with 250 ml of dichloromethane each time. After concentrating in vacuo, the product is dried in a high vacuum.

Yield: 24.8 g (77% of theory); $R_f$=0.78 (PE/EA 4:1)

EXAMPLE IV

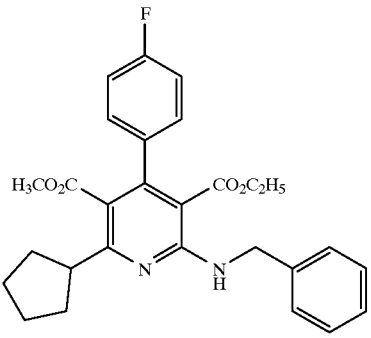

26 g (64 mmol) of the compound from Example III, 14 ml (130 mmol) of benzylamine and 17 g (160 mmol) of sodium carbonate are stirred under reflux for 2 days in 220 ml of acetonitrile. A further 6.9 ml (64 mmol) of benzylamine and 6.8 g (64 mmol) of sodium carbonate are added and the mixture is stirred under reflux for a further 20 hours. After cooling to room temperature, the mixture is filtered off with suction through silica gel and the solid is washed with 100 ml of ethyl acetate. After concentrating in vacuo, the partially crystallizing residue is taken up in 100 ml of petroleum ether with stirring. The precipitated solid is filtered off with suction, washed with some petroleum ether and dried in a high vacuum. The mother liquor which remains is concentrated and chromatographed on silica gel (200 g of silica gel 230–400 mesh, d=3.5 cm, eluent toluene).

Yield: 25.1 g (82% of theory); $R_f$=0.54 (PE/EA 8:1)

EXAMPLE V

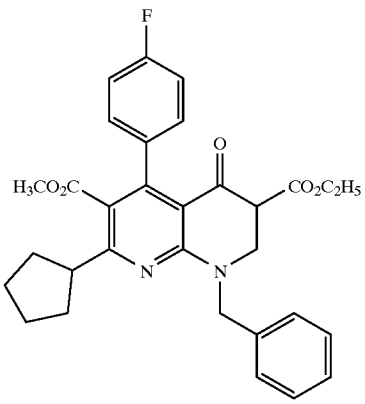

8.1 g (17 mmol) of the compound from Example IV are dissolved in 60 ml of absolute THF under argon. 2.4 g (21.2 mmol) of potassium tert-butoxide are added to this solution at 0° C. and the mixture is stirred at this temperature for 15 min. 2.30 ml (21.2 mmol) of ethyl acrylate are then added dropwise at 0° C. and the mixture is stirred at room temperature for 16 hours. 0.39 g (3.4 mmol) of potassium tert-butoxide and 0.37 g (3.4 mmol) of ethyl acrylate are again added to the solution. It is stirred at room temperature for a further 20 hours. The reaction mixture is then added to 100 ml of ice water and acidified using 20 ml of 2 molar hydrochloric acid. It is extracted twice with 100 ml of ethyl acetate each time, and the combined organic phases are dried over sodium sulphate and concentrated in vacuo. The residue is chromatographed on silica gel (250 g of silica gel 230–400 mesh, d=3.5 cm, eluent petroleum ether/ethyl acetate 12:1).

Yield: 7.64 g (90% of theory); $R_f$=0.38 (PE/EA 8:1)

EXAMPLE VI

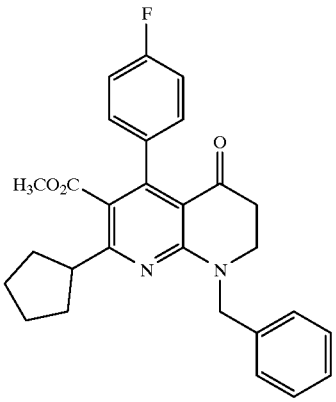

7.64 g (15.32 mmol) of the compound from Example V are heated under reflux for 3 hours in ethanol with addition of 9.8 ml (36.78 mmol) of 15% strength sodium hydroxide solution. After cooling to room temperature, the mixture is concentrated in vacuo and the residue is treated with 50 ml each of dichloromethane and water. The aqueous phase is extracted with 50 ml of dichloromethane and the combined organic phases are dried over sodium sulphate. After concentrating in vacuo, the residue which remains is chromatographed on silica gel (250 g of silica gel 230–400 mesh, d=3.5 cm, eluent petroleum ether/ethyl acetate 8:1).

Yield: 5.74 g (82% of theory); $R_f$=0.52 (PE/EA 4:1)

EXAMPLE VII

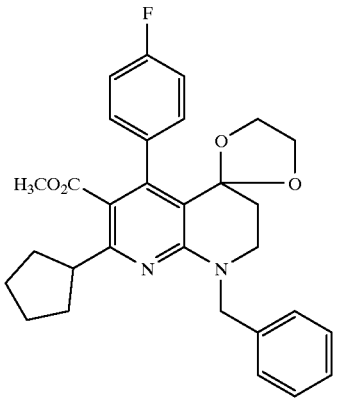

5.70 g (12.4 mmol) of the compound from Example VI, 10 ml of 1,2-ethanediol and 0.15 g (0.79 mmol) of p-toluenesulphonic acid are heated under reflux in a water separator for 20 hours in 200 ml of benzene. After cooling to room temperature, the mixture is treated with 50 ml of saturated sodium hydrogen carbonate solution. The organic phase is washed once with water, dried over sodium sulphate and concentrated in vacuo. The solid remaining is recrystallized from pentane/diethyl ether.

Yield: 5.47 g (88% of theory); $R_f$=0.37 (PE/EA 8:1)

EXAMPLE VIII

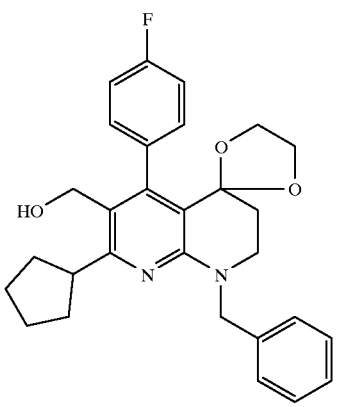

5.47 g (10.90 mmol) of the compound from Example VII are dissolved in 40 ml of absolute THF under argon. 21.79 ml of lithium aluminium hydride (1 molar solution in THF) are added dropwise at 0° C. to this solution. It is subsequently stirred at room temperature for 20 hours and then cooled to 0° C. 40 ml of water are added at this temperature. The aqueous phase is extracted twice using 40 ml of ethyl acetate each time. The combined organic phases are washed once with 40 ml of saturated sodium chloride solution, dried over sodium sulphate and concentrated in vacuo. The residue is chromatographed on silica gel (250 g of silica gel 230–400 mesh, d=3.5 cm, eluent petroleum ether/ethyl acetate 8:1).

Yield: 3.55 g (69% of theory); $R_f$=0.46 (PE/EA 4:1)

EXAMPLE IX

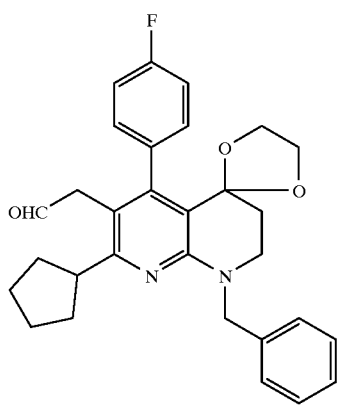

3.20 g (6.74 mmol) of the compound from Example VIII are dissolved in 30 ml of absolute dichloromethane under argon. 3.24 g (8.43 mmol) of pyridinium dichromate are introduced into this solution at −10° C. in small portions. After stirring at room temperature for 5 hours, the reaction mixture is filtered off with suction through 20 g of silica gel (230–400 mesh), washed twice with 30 ml of dichloromethane each time and concentrated in vacuo.

Yield: 1.39 (44% of theory); $R_f$=0.66 (PE/EA 4:1)

EXAMPLE X

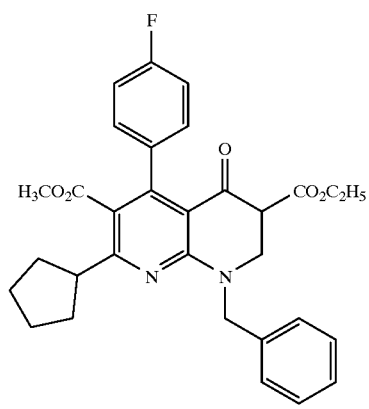

12.5 g (23.7 mmol) of the compound from Example V and 20 g (230 mmol) of manganese dioxide are vigorously stirred under reflux for 2.5 hours in 250 ml of ethyl acetate. After cooling to room temperature, the mixture is filtered through kieselguhr and concentrated in vacuo.

Yield: 10.75 g (86% of theory); $R_f$=0.40 (PE/EA 2:1)

EXAMPLE XI

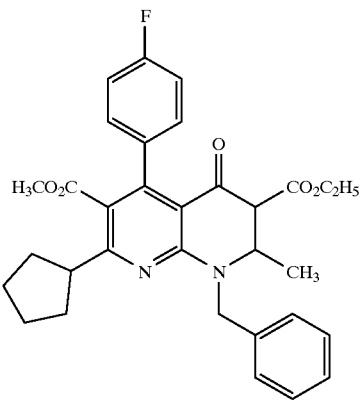

5.0 g (9.46 mmol) of the compound from Example X are dissolved in 60 ml of absolute THF under argon. 3.5 ml of methylmagnesium bromide solution (3 molar solution in diethyl ether) are added dropwise at −78° C. in the course of 30 min. The mixture is stirred at −78° C. for 2 hours and subsequently at −50° C. for 1 hour. The reaction mixture is treated with 30 ml of phosphate buffer solution (pH 7) and warmed to room temperature. After separating off the organic phase, the aqueous phase is extracted once with 50 ml of ethyl acetate. The combined organic phases are dried over sodium sulphate and concentrated in vacuo. The residue is chromatographed on silica gel (200 g of silica gel 230–400 mesh, d=3.5 cm, eluent petroleum ether/ethyl acetate 10:1).

Yield: 2.25 g (diastereomer mixture) (46% of theory); $R_f$=diastereomer A: 0.80 (PE/EA 8:1) $R_f$=diastereomer B: 0.69 (PE/EA 8:1)

EXAMPLE XII

Ethyl [benzyl-(2-oxo-propyl)-amino]-acetate

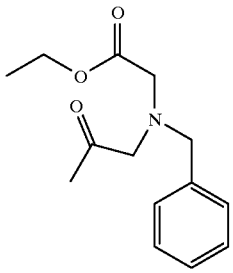

96.6 g (500 mmol) of ethyl benzylamino-acetate and 42.0 g (500 mmol) of sodium hydrogen carbonate are heated to 55° C. in 400 ml of ethanol and treated with 46.6 g (500 mmol) of chloroacetone in the course of 1 hour. The mixture is stirred at 60° C. for 18 hours and subsequently cooled to room temperature. The solid is filtered off with suction and washed with 100 ml of ethanol. The filtrate is concentrated in vacuo and the residue which remains is treated with 125 ml of 1 molar sodium hydroxide solution with ice-cooling. 17.4 g (124 mmol) of benzoyl chloride are then added and the mixture is stirred vigorously for 10 min. It is acidified to pH 1.5 using 1 molar hydrochloric acid and extracted 3 times with 50 ml of diethyl ether each time. The combined organic phases are washed twice with 50 ml of 1 molar hydrochloric acid in each case. The combined aqueous phases are adjusted to pH 7.5 using 1 molar sodium hydroxide solution and extracted three times with 100 ml of diethyl ether each time. The combined organic phases are dried over sodium sulphate and concentrated in vacuo.

Yield: 77.3 g (62% of theory); $R_f$=0.36 (PE/EA 4:1)

EXAMPLE XIII

1-Benzyl-piperidine-3,5-dione

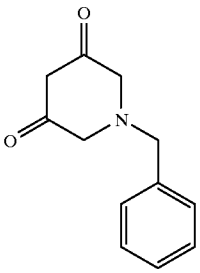

38.3 g (341 mmol) of potassium tert-butoxide are dissolved under argon in 500 ml of absolute diethyl ether and 500 ml of tert-butanol. A solution of 77.3 g (310 mmol) of the compound from Example XII in 100 ml of diethyl ether is then added at −15° C. and the mixture is stirred at room temperature for 18 hours. It is concentrated not quite to dryness at a bath temperature of 30° C. and the residue is taken up under argon using 500 ml of an absolute diethyl ether. The solid is filtered off with suction and washed with 100 ml of absolute diethyl ether. The solid is then dissolved in 260 ml of 2 molar acetic acid. After addition of 90 ml of water, the desired product precipitates. To complete the crystallization, the mixture is allowed to stand at 5° C. for 18 hours. The solid is filtered off with suction, washed with 50 ml of ice water and dried over phosphorus pentoxide in vacuo for 24 hours.

Yield: 46.1 g (73% of theory); $R_f$=0.36 (dichloromethane/methanol/glacial acetic acid 3:1:0.1)

EXAMPLE XIV

Methyl 7-benzyl-2-cyclopentyl-4-(4-fluorophenyl)-5-oxo-1,4,5,6,7,8-hexahydro-[1,7]-naphthyridine-3-carboxylate

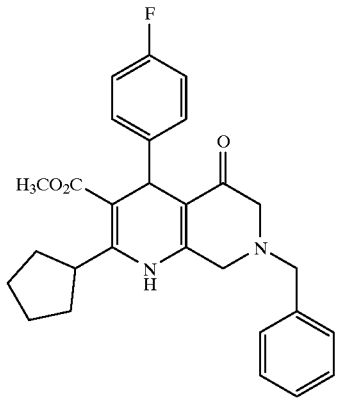

15.4 g (76 mmol) of the compound from Example XIII, 9.4 g (76 mmol) of 4-fluorobenzaldehyde and 12.8 g (76 mmol) of methyl 3-amino-3-cyclopentyl-prop-2-ene-carboxylate are heated under reflux for 18 hours in 150 ml

EXAMPLE XV

Methyl 7-benzyl-2-cyclopentyl-4-(4-fluorophenyl)-5-oxo-5,6,7,8-tetrahydro-[1,7]-naphthyridine-3-carboxylate

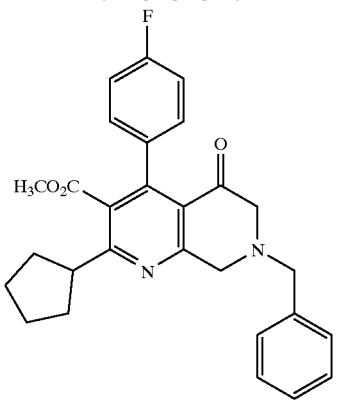

11.2 g (24 mmol) of the compound from Example XIV are dissolved in 300 ml of absolute dichloromethane and treated with 6.1 g (26.7 mmol) of 2,3-dichloro-5,6-dicyano-p-benzoquinone. The mixture is stirred at room temperature for 3 hours and then filtered off with suction through 400 g of silica gel (230–400 mesh). The silica gel is washed with 5 l of dichloromethane and the combined organic phases are concentrated in vacuo.

Yield: 7.9 g (71% of theory); $R_f$=0.50 (PE/EA 6:1)

EXAMPLE XVI

Methyl 7-benzyl-2-cyclopentyl-4-(4-fluorophenyl)-5-hydroxy-5,6,7,8-tetrahydro-[1,7]-naphthyridine-3-carboxylate

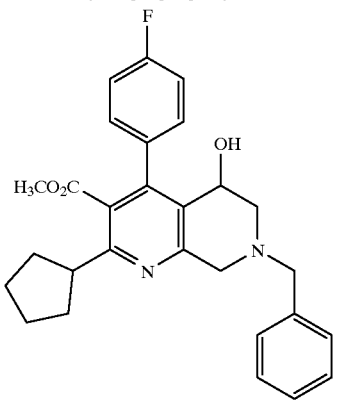

5.5 g (12 mmol) of the compound from Example XV are dissolved under argon in 100 ml of methanol and treated at 0° C. with 0.91 g (24 mmol) of sodium borohydride. The mixture is stirred at 0° C. for 20 min and subsequently at room temperature for 1 hour. The reaction solution is treated with 100 ml of saturated ammonium chloride solution and extracted three times with 100 ml of ethyl acetate each time. The combined organic phases are washed with 50 ml of saturated sodium chloride solution, dried over sodium sulphate and concentrated in vacuo. The residue is chromatographed on silica gel (400 g of silica gel 230–400 mesh, d=4.5 cm, eluent petroleum ether/ethyl acetate 4:1).

Yield: 4.6 g (83% of theory); $R_f$=0.36 (PE/EA 6:1)

EXAMPLE XVII

Methyl 7-benzyl-5-tert-butyldimethylsiloxy-2-cyclopentyl-4-(4-fluorophenyl)-5,6,7,8-tetrahydro-[1,7]-naphthyridine-3-carboxylate

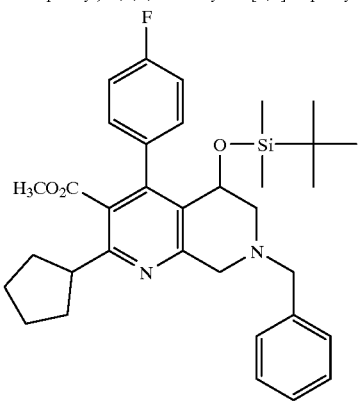

4.6 (10.0 mmol) of the compound from Example XVI are dissolved under argon in 40 ml of absolute DMF and treated at room temperature with 2.5 g (36 mmol) of imidazole, 3.0 g (20 mmol) of tert-butyldimethylchlorosilane and 0.02 g (0.2 mmol) of dimethylaminopyridine. The mixture is stirred at room temperature for 3 days and then partitioned between 100 ml of saturated ammonium chloride solution and 100 ml of toluene with stirring. The aqueous phase is extracted twice more with 100 ml of toluene each time, and the combined organic phases are washed twice with 25 ml of water, dried over sodium sulphate and concentrated in vacuo. The residue is chromatographed on silica gel (400 g of silica gel 230–400 mesh, d=4.5 cm, eluent petroleum ether/ethyl acetate 20:1).

Yield: 5.7 g (99% of theory); $R_f$=0.21 (PE/EA20:1)

EXAMPLE XVIII

7-Benzyl-5-tert-butyldimethylsiloxy-2-cyclopentyl-4-(4-fluorophenyl)-3-hydroxymethyl-5,6,7,8-tetrahydro-[1,7]-naphthyridine

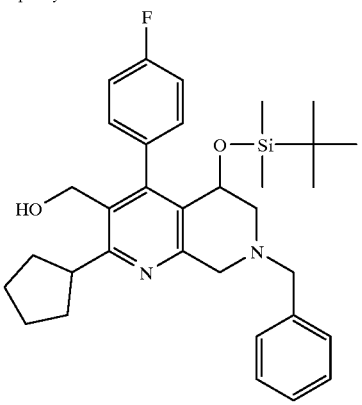

3.0 g (5.2 mmol) of the compound from Example XVII are dissolved under argon in 60 ml of absolute toluene. 15.7 ml of diisobutylaluminium hydride solution (1 molar in toluene) are added dropwise at −78° C. and the mixture is stirred at this temperature for 18 hours. 5 ml of methanol and then 20 ml of a 20% strength sodium potassium tartrate solution are subsequently added at −78° C. The mixture is warmed to room temperature and extracted twice with 50 ml of ethyl acetate each time. The combined organic phases are washed once each with 20 ml of water and 20 ml of saturated sodium chloride solution, dried over sodium sulphate and concentrated in vacuo. The residue is chromatographed on silica gel (200 g of silica gel 230–400 mesh, d=3.5 cm, eluent petroleum ether/ethyl acetate 6:1).

Yield: 1.67 g (59% of theory); $R_f$=0.53 (PE/EA 4:1)

EXAMPLE XIX

7-Benzyl-5-tert-butyldimethylsiloxy-2-cyclopentyl-4-(4-fluorophenyl)-5,6,7,8-tetrahydro-[1,7]-naphthyridine-3-carbaldehyde

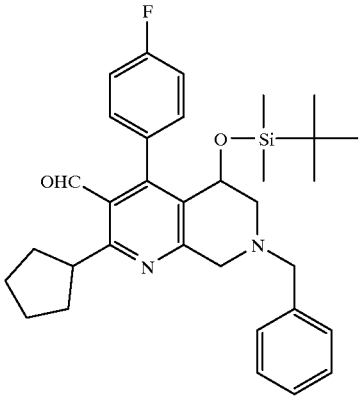

1.6 g (3.0 mmol) of the compound from Example XVIII are treated with 1.5 g (15 mmol) of triethylamine and 4 ml of dimethyl sulphoxide at room temperature in 15 ml of absolute dichloromethane. The solution is cooled to 0° C. and treated with 1.9 g (12 mmol) of sulphur trioxide-pyridine complex. The mixture is stirred at 0° C. for 3 hours and then treated again with 1.5 g (15 mmol) of triethylamine, 4 ml of dimethyl sulphoxide and 1.9 g (12 mmol) of sulphur trioxide-pyridine complex. The solution is stirred at 10° C. for 1 hour and then treated with 20 ml of ice water. After separation of the phases, the aqueous phase is extracted once with 20 ml of dichloromethane. The combined organic phases are washed with 10 ml of water and saturated sodium chloride solution in each case, dried over sodium sulphate and concentrated in vacuo. The residue is chromatographed on silica gel (200 g of silica gel 230–400 mesh, d=3.5 cm, eluent petroleum ether/ethyl acetate 8:1).

Yield: 1.4 g (86% of theory); $R_f$=0.91 (PE/EA 4:1)

PREPARATION EXAMPLES

EXAMPLE 1

1-Benzyl-7-cyclopentyl-4,4-(1,2-ethanedioxy)-5-(4-fluorophenyl)-6-[hydroxy-(4-trifluoromethyl-phenyl)-methyl]-1,2,3,4-tetrahydro-[1,8]-naphthyridine

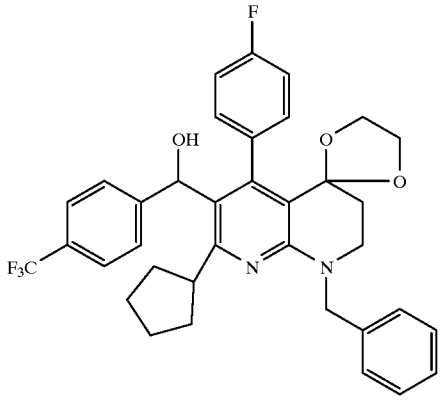

0.49 g (20 mmol) of magnesium turnings is heated to 60° C. under argon in 50 ml of absolute THF and treated with a solution of 1.89 ml (13 mmol) of 4-bromobenzotrifluoride in 8 ml of absolute THF in the course of 20 min. The mixture is heated under reflux for 2 hours and then cooled to room temperature (Grignard reagent solution). A solution of 1.39 g (2.94 mmol) of the compound from Example IX is treated with 50 ml of the Grignard reagent solution under argon at 0° C. in 20 ml of absolute THF. The mixture is then stirred at room temperature for 1 hour. The reaction mixture is partitioned in 100 ml of phosphate buffer solution (pH 7) and 100 ml of ethyl acetate with stirring, the organic phase is separated off and the aqueous phase is extracted twice with 50 ml of ethyl acetate each time. The combined organic phases are dried over sodium sulphate and concentrated in vacuo. The residue is chromatographed on silica gel (200 g of silica gel 230–400 mesh, d=3.5 cm, eluent petroleum ether/ethyl acetate 6:1).

Yield: 1.71 g (94% of theory); $R_f$=0.42 (PE/EA 4:1)

EXAMPLE 2

1-Benzyl-7-cyclopentyl-5-(4-fluorophenyl)-6-[hydroxy-(4-trifluoromethyl-phenyl)-methyl]-4-oxo-1,2,3,4-tetrahydro-[1,8]-naphthyridine

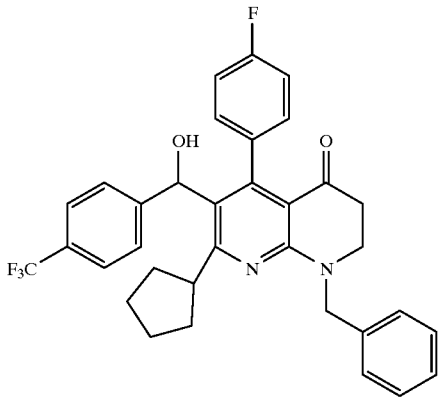

A solution of 1.71 g (2.76 mmol) of the compound from Example 1 in 40 ml of absolute acetone is treated at room temperature with 27 mg (0.14 mmol) of p-toluene-sulphonic acid and 1 ml of water and stirred for 1 hour. The reaction solution is dried over sodium sulphate and filtered through 30 g of silica gel (230–400 mesh). It is washed with 50 ml of dichloromethane and the combined organic filtrates are concentrated in vacuo.

Yield: 1.51 (95% of theory); $R_f$=0.32 (PE/EA 4:1)

EXAMPLE 3

1-Benzyl-7-cyclopentyl-5-(4-fluorophenyl)-6-[hydroxy-(4-trifluoromethyl-phenyl)-methyl]-1,2,3,4-tetrahydro-[1,8]-naphthyridin-4-ol

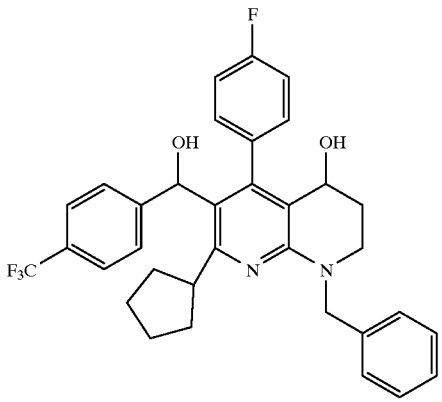

0.80 g (1.39 mmol) of the compound from Example 2 is dissolved under argon in 30 ml of absolute THF and treated at −78° C. with 4.17 ml of diisobutylaluminium hydride (1 molar solution in THF). The mixture is stirred at −78° C. for 1 hour and then treated with 10 ml of saturated sodium sulphate solution. After warming to room temperature, the organic phase is separated off and the aqueous phase is extracted twice with 30 ml of ethyl acetate in each case. The combined organic phases are dried over sodium sulphate and concentrated in vacuo. The residue is chromatographed on silica gel (100 g of silica gel 230–400 mesh, d=2.5 cm, eluent cyclohexane/ethyl acetate 6:1).

Yield of diastereomer A: 0.37 g (45% of theory); $R_f$=0.46 (PE/EA 4:1) Yield of diastereomer B: 0.39 g (48% of theory) $R_f$=0.19 (PE/EA 4:1)

EXAMPLE 4

7-Benzyl-5-tert-butyldimethylsiloxy-2-cyclopentyl-4-(4-fluorophenyl)-3-[hydroxy-(4-trifluoromethyl-phenyl)-methyl]-5,6,7,8-tetrahydro-[1,7]-naphthyridine

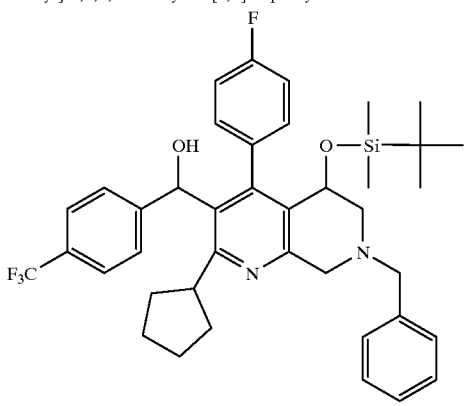

0.21 g (7.7 mmol) of magnesium turnings is heated under argon to 60° C. in 20 ml of absolute THF and treated with a solution of 1.7 g (7.7 mmol) of 4-bromobenzotrifluoride in 8 ml of absolute THF in the course of 20 min. The mixture is heated under reflux for 2 hours and then cooled to room temperature (Grignard reagent solution). A solution of 1.40 g (2.6 mmol) of the compound from Example XIX is treated with 20 ml of the Grignard reagent solution under argon at 0° C. in 22 ml of absolute THF. It is then stirred at room temperature for 1 hour. The reaction mixture is partitioned in 50 ml of phosphate buffer solution (pH 7) and 50 ml of ethyl acetate with stirring, the organic phase is separated off and the aqueous phase is extracted twice with 50 ml of ethyl acetate each time. The combined organic phases are dried over sodium sulphate and concentrated in vacuo. The residue is chromatographed on silica gel (250 g of silica gel 230–400 mesh, d=3.5 cm, eluent petroleum ether/ethyl acetate 6:1).

Yield of diastereomer A: 0.68 g (38% of theory); $R_f$ (diastereomer A)=0.55 (PE/EA 6:1) Yield of diastereomer B: 0.50 g (28% of theory) $R_f$ (diastereomer B)=0.33 (PE/EA 6:1)

EXAMPLE 5

7-Benzyl-5-tert-butyldimethylsiloxy-2-cyclopentyl-4-(4-fluorophenyl)-3-[fluoro-(4-trifluoromethyl-phenyl)-methyl]-5,6,7,8-tetrahydro-[1,7]-naphthyridine

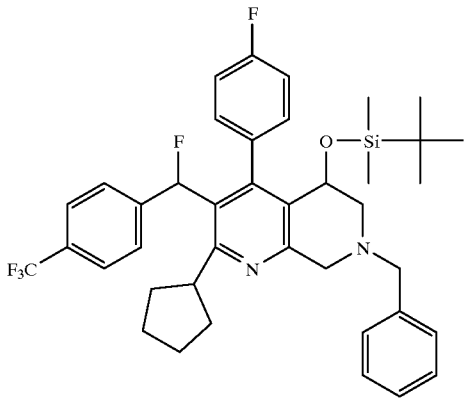

200 mg (0.3 mmol) of the compound from Example 4 (diastereomer A) are dissolved under argon in 6 ml of absolute dichloromethane. 0.06 ml (0.45 mmol) of diethylaminosulphur trifluoride is added dropwise at −30° C. and the mixture is stirred at this temperature for 1 more hour. The reaction solution is then added to 20 ml of ice-cold, saturated sodium hydrogen carbonate solution. It is extracted three times with 20 ml of dichloromethane each time. The combined organic phases are dried over sodium sulphate and concentrated in vacuo.

Yield: 193 mg (93% of theory); $R_f$=0.82 (PE/EA 4:1)

EXAMPLE 6

7-Benzyl-2-cyclopentyl-4-(4-fluorophenyl)-3-[fluoro-(4-trifluoromethyl-phenyl)-methyl]-5,6,7,8-tetrahydro-[1,7]-naphthyridin-5-ol

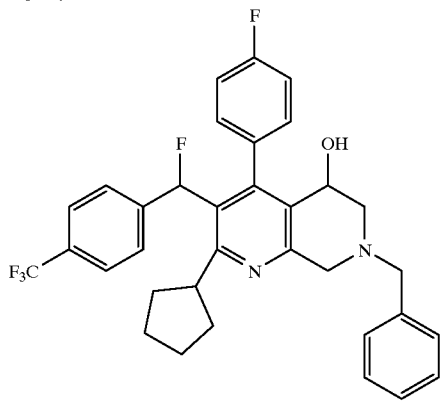

90 mg (0.13 mmol) of the compound from Example 5 are dissolved in 3 ml of THF and 3 ml of methanol at room temperature. 1.3 ml of a 3 molar hydrochloric acid are added to this solution and it is stirred at room temperature for 18 hours. The reaction mixture is added to 10 ml of saturated sodium hydrogen carbonate solution and extracted three times with 20 ml of ethyl acetate each time. The combined organic phases are washed once with 10 ml of a saturated sodium chloride solution, dried over sodium sulphate and concentrated in vacuo. The residue is chromatographed on silica gel (10 g of silica gel 230–400 mesh, d=2 cm, eluent petroleum ether/ethyl acetate 6:1).

Yield: 28 mg (37% of theory); $R_f$=0.60 (PE/EA 4:1)

The compounds listed in Tables 1, 2, 3, 4, 5 and 6 are prepared in analogy to the abovementioned procedures.

TABLE 1

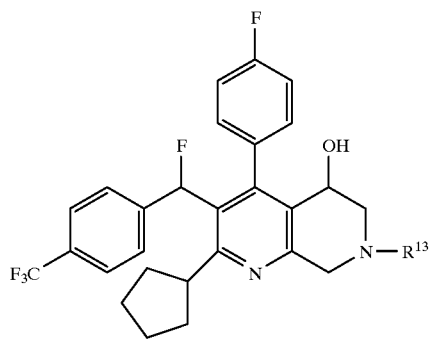

| Ex. No. | $R^{13}$ | Isomer | $R_f$ |
|---|---|---|---|
| 7 | $CH_2$—$C_6H_5$ | Diastereomer 1 | 0.65 PE:EA (4:1) |
| 8 | $CH_3$ | | 0.18 PE:EA (1:1) |
| 9 | H | | 0.14 $CH_2CL_2$:MeOH:$NH_3$ (20:1:0.1) |
| 10 | $(CH_2)_3$—$CH_3$ | | 0.51 PE:EA (4:1) |

TABLE 2

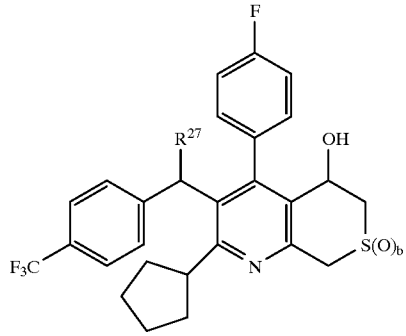

| Ex. No. | $R^{27}$ | b | Isomer | $R_f$ |
|---|---|---|---|---|
| 11 | F | 0 | Mixture | 0.568 Tol/EA (9:1) |
| 12 | F | 0 | | 0.584 Tol/EA (9:1) |
| 13 | F | 2 | Mixture | 0.23 Tol/EA (9:1) |
| 14 | OH | 2 | Mixture | 0.058 Tol/EA (9:1) |
| 15 | F | 2 | Isomer II | 0.183 Tol/EA (9:1) |

TABLE 3
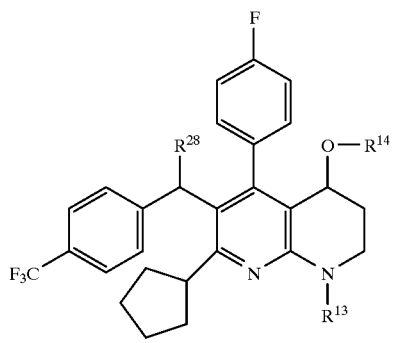
| Ex. No. | $R^{28}$ | $R^{14}$ | $R^{13}$ | Isomer | $R_f$ |
|---|---|---|---|---|---|
| 16 | H | H | CH$_2$—C$_6$H$_5$ | Racemate | 0.35 PE:EA (8:1) |
| 17 | OH | H | H | Diastereomer 1 | 0.21 PE:EA (2:1) |
| 18 | H | C$_2$H$_5$ | H | Racemate | 0.54 PE:EA (2:1) |
| 19 | H | H | H | Racemate | 0.28 PE:EA (2:1) |
TABLE 4
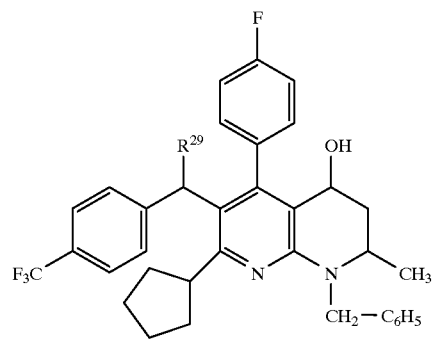
| Ex. No. | $R^{29}$ | Isomer | $R_f$ | Yield (% of theory) |
|---|---|---|---|---|
| 20 | H | Diastereomer 1 (Racemate) | 0.31 PE:EA (8:1) | |
| 21 | OH | Diastereomer 1 | 0.37 PE:EA (4:1) | |
| 22 | OH | Diastereomer 2 | 0.21 PE:EA (4:1) | |
TABLE 5
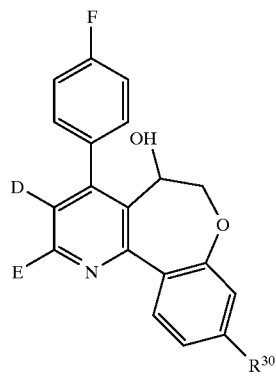
| Ex. No. | D | E | $R^{30}$ | Isomer | $R_f$ |
|---|---|---|---|---|---|
| 23 | ![4-(1-fluoroethyl)-trifluoromethylphenyl] | H$_3$C—CH(CH$_3$)— | OCH$_3$ | | 0.30 PE/EA 6:1 |

TABLE 6

[Structure: 4-(4-fluorophenyl)-8-cyclopentyl-7-[(4-trifluoromethylphenyl)(R³¹)methyl]-6-benzyl-5,6,7,8-tetrahydro-1,6-naphthyridin-4-ol with N—CH₂—C₆H₅]

| Ex. No. | R³¹ | Isomer | $R_f$ |
|---|---|---|---|
| 24 | H | Racemate | 0.38 PE/EA 6:1 |

The compounds listed in Table 7 are prepared in analogy to the abovementioned procedures:

TABLE 7

| Ex. No. | Structure | Isomer | $R_f$ value |
|---|---|---|---|
| 25 | [Structure with OCH₂CH₂OH, F, CF₃, cyclopentyl, CH₃, benzyl] | Diastereomer mixture | 0.34 Pentane/Ether 2:1 |
| 26 | [Structure with OH, F, CF₃, cyclopentyl, CH₃, benzyl] | Diastereomer 2 (Racemate) | 0.49 PE/EA 4:1 |

TABLE 7-continued

| Ex. No. | Structure | Isomer | $R_f$ value |
| --- | --- | --- | --- |
| 27 | 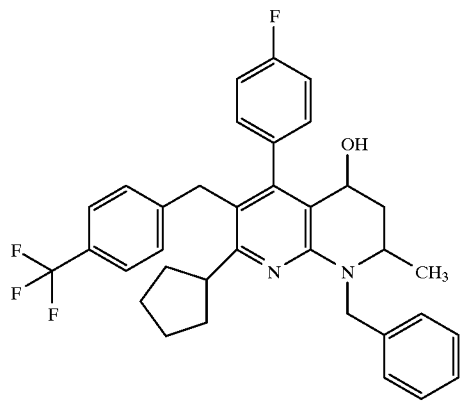 | Diastereomer 1<br>Enantiomer 1 | 0.32<br>PE/EA 9:1 |
| 28 | 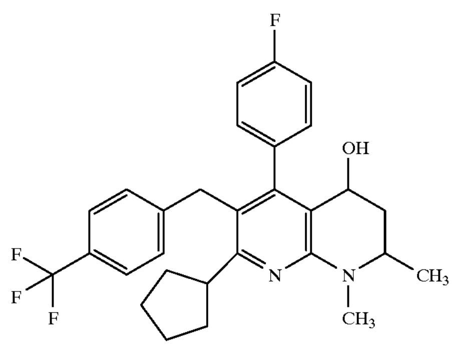 | Diastereomer 1<br>(Racemate) | 0.53<br>CH/EA 4:1 |
| 29 | 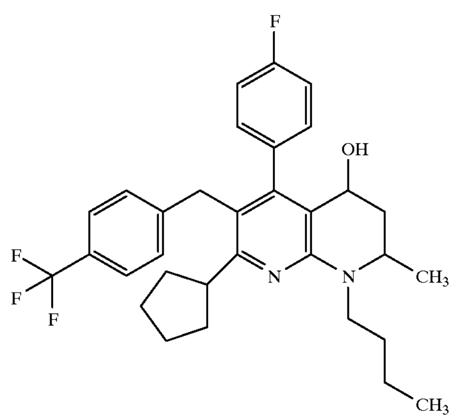 | Diastereomer 1<br>(Racemate) | 0.53<br>CH/EA 4:1 |
| 30 | 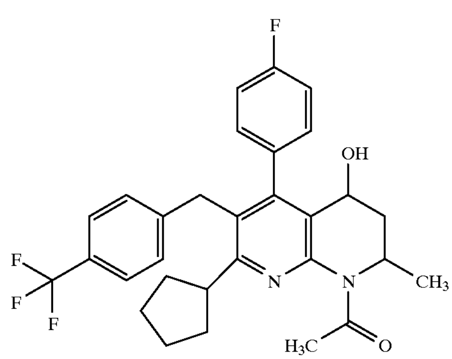 | Diastereomer 1<br>(Racemate) | 0.19<br>CH/EA 4:1 |

TABLE 7-continued

| Ex. No. | Structure | Isomer | R_f value |
|---|---|---|---|
| 31 | 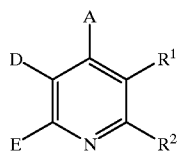 | Racemate | 0.58<br>CH/EA 4:1 |

We claim:

1. Heterocyclic-fused pyridines of the formula (I)

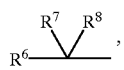

(I)

in which

A represents aryl having 6 to 10 carbon atoms, which is optionally substituted up to 5 times in an identical or different manner by halogen, hydroxyl, trifluoromethyl, trifluoromethoxy, nitro or by straight-chain or branched alkyl, acyl, hydroxyalkyl or alkoxy each having up to 7 carbon atoms, or by a group of the formula —NR$^3$R$^4$, in which
$R^3$ and $R^4$ are identical or different and denote hydrogen, phenyl or straight-chain or branched alkyl having up to 6 carbon atoms, D represents a radical of the formula
$R^5$—X— or in which
$R^5$ and $R^6$ independently of one another denote cycloalkyl having 3 to 8 carbon atoms, or aryl having 6 to 10 carbon atoms,
or a 5- to 7-membered aromatic, optionally benzo-fused heterocycle having up to 3 heteroatoms from the series consisting of S, N and/or O, each of which is optionally substituted up to 5 times in an identical or different manner by trifluoromethyl, nitro, trifluoromethoxy, halogen, hydroxyl, carboxyl, by straight-chain or branched alkyl, acyl, alkoxy or alkoxycarbonyl each having up to 6 carbon atoms or by phenyl, phenoxy or thiophenyl, which for their part can be substituted by halogen, trifluoromethyl or trifluoromethoxy,
or the cycles are optionally substituted by a group of the formula —NR$^9$R$^{10}$,
in which
$R^9$ and $R^{10}$ are identical or different and have the meaning of $R^3$ and $R^4$ indicated above, X denotes straight-chain or branched alkylene or alkenylene each having up to 8 carbon atoms, each of which is optionally substituted up to 2 times by hydroxyl, $R^7$ denotes hydrogen or halogen and
$R^8$ denotes hydrogen, halogen, azido, trifluoromethyl, hydroxyl, trifluoromethoxy, straight-chain or branched alkoxy having up to 5 carbon atoms or a radical of the formula —NR$^{11}$R$^{12}$,
in which
$R^{11}$ and $R^{12}$ are identical or different and have the meaning of $R^3$ and $R^4$ indicated above, or
$R^7$ and $R^8$, together with the C atom, form a carbonyl group, E represents cycloalkyl having 3 to 8 carbon atoms, or represents straight-chain or branched alkyl having up to 8 carbon atoms, which is optionally substituted by cycloalkyl having 3 to 8 carbon atoms or by hydroxyl, $R^1$ and $R^2$ together form an alkylene chain having up to 6 carbon atoms, which is interrupted by an oxygen or sulphur atom or by the group —SO$_2$— or —NR$^{13}$,
where
$R^{13}$ denotes hydrogen or straight-chain or branched alkyl or acyl each having up to 6 carbon atoms, or denotes benzyl or phenyl, each of which is optionally substituted up to 2 times in an identical or different manner by halogen, hydroxyl, nitro, trifluoromethyl or straight-chain or branched alkyl or acyl each having up to 6 carbon atoms, and where the heterocyclic ring thus formed, which can also be benzo-fused and can contain a double bond, must always be substituted by a carbonyl group or a radical of the formula

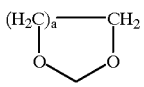

or —OR$^{14}$,
in which
a denotes a number 1, 2 or 3 and
R$^{14}$ denotes hydrogen or straight-chain or branched alkyl, hydroxy-substituted alkyl, acyl or alkoxycarbonyl each having up to 6 carbon atoms or a radical of the formula —SiR$^{15}$R$^{16}$R$^{17}$,
in which
R$^{15}$, R$^{16}$ and R$^{17}$ are identical or different and denote phenyl, straight-chain or branched alkyl having up to 6 carbon atoms,
and the heterocyclic and/or benzo-fused ring (R$^1$/R$^2$) is optionally substituted up to 5 times in an identical or different manner, optionally also geminally, by straight-chain or branched alkoxy or alkoxycarbonyl each having up to 6 carbon atoms, trifluoromethyl, halogen, hydroxyl, carbonyl or phenyl which, for its part, can be substituted by halogen, trifluoromethyl, nitro, hydroxyl or by straight-chain or branched alkyl, alkoxy or alkoxycarbonyl each having up to 6 carbon atoms,
and/or is optionally substituted up to 6 times, optionally also geminally, in an identical or different manner by cycloalkyl or cycloalkyloxy each having 3 to 8 carbon atoms or by straight-chain or branched alkyl having up to 6 carbon atoms, which for its part can be substituted by hydroxyl, trifluoromethyl, phenyl or by straight-chain or branched alkoxy having up to 5 carbon atoms,
and/or is optionally substituted by a spiro-linked radical of the formula

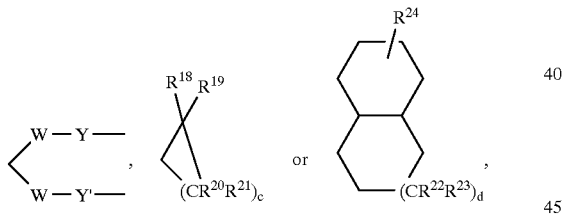

in which
W denotes either an oxygen or a sulphur atom,
Y and Y' together form a 2- to 6-membered straight-chain or branched alkylene chain,
c denotes a number 1, 2, 3, 4, 5, 6 or 7,
d denotes a number 1 or 2,
R$^{18}$, R$^{19}$, R$^{20}$, R$^{21}$, R$^{22}$, R$^{23}$ and R$^{24}$ are identical or different and denote hydrogen, trifluoromethyl, phenyl, halogen or straight-chain or branched alkyl or alkoxy each having up to 6 carbon atoms or
R$^{18}$ and R$^{19}$ or R$^{20}$ and R$^{21}$ in each case together form a straight-chain or branched alkylene chain having up to 6 carbon atoms or
R$^{18}$ and R$^{19}$ or R$^{20}$ and R$^{21}$ in each case together form a radical of the formula

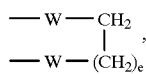

in which
W has the meaning indicated above,
e denotes a number 1, 2, 3, 4, 5, 6 or 7,
and their salts and N-oxides.

2. Heterocyclic-fused pyridines of the formula according to claim 1
in which
A represents naphthyl or phenyl, each of which is optionally substituted up to 3 times in an identical or different manner by fluorine, chlorine, bromine, hydroxyl, trifluoromethyl, trifluoromethoxy, nitro or by straight-chain or branched alkyl, acyl or alkoxy each having up to 6 carbon atoms or by a group of the formula —NR$^3$R$^4$,
in which
R$^3$ and R$^4$ are identical or different and denote hydrogen, phenyl or straight-chain or branched alkyl having up to 4 carbon atoms,
D represents a radical of the formula
R$^5$—X— or

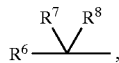

in which
R$^5$ and R$^6$ independently of one another
denote cyclopropyl, cyclopentyl or cyclohexyl, or denote naphthyl, phenyl, pyridyl, quinolyl, indolyl, benzothiazolyl or tetrahydronaphthalenyl, each of which is optionally substituted up to 3 times in an identical or different manner by trifluoromethyl, trifluoromethoxy, fluorine, chlorine, bromine, hydroxyl, carboxyl, by straight-chain or branched alkyl, acyl, alkoxy or alkoxycarbonyl each having up to 5 carbon atoms or by phenyl, phenoxy or thiophenyl, which for their part can be substituted by fluorine, chlorine, bromine, trifluoromethyl or trifluoromethoxy,
or the cycles are optionally substituted by a group of the formula —NR$^9$R$^{10}$,
in which
R$^9$ and R$^{10}$ are identical or different and have the meaning of R$^3$ and R$^4$ indicated above,
X denotes straight-chain or branched alkylene or alkenylene each having up to 6 carbon atoms, each of which is optionally substituted up to 2 times by hydroxyl,
R$^7$ denotes hydrogen, fluorine or chlorine, and
R$^8$ denotes hydrogen, fluorine, chlorine, bromine, azido, trifluoromethyl, hydroxyl, trifluoromethoxy, straight-chain or branched alkoxy having up to 4 carbon atoms or a radical of the formula —NR$^{11}$R$^{12}$,
in which
R$^{11}$ and R$^{12}$ are identical or different and have the meaning of R$^3$ and R$^4$ indicated above, or
R$^7$ and R$^8$ together with the C atom form a carbonyl group,
E represents cyclopropyl, cyclobutyl, cyclopentyl, cyclohexyl or cycloheptyl, or represents straight-chain or branched alkyl having up to 6 carbon atoms, which is optionally substituted by cyclopropyl, cyclobutyl, cyclopentyl, cyclohexyl, cycloheptyl or by hydroxyl,
R$^1$ and R$^2$ together form an alkylene chain having up to 5 carbon atoms, which is interrupted by an oxygen or sulphur atom or by the group —SO$_2$— or —NR$^{13}$, where $R^{13}$ denotes hydrogen or straight-chain or branched alkyl or acyl each having up to 5 carbon atoms, or denotes benzyl or phenyl, each of which is optionally substituted up to 2 times in an identical or different manner by fluorine, chlorine, bromine, hydroxyl, nitro, trifluoromethyl or straight-chain or branched alkyl or acyl each having up to 4 carbon atoms, and where the heterocyclic ring thus formed, which can also be benzo-fused and can contain a double bond, must always be substituted by a carbonyl group or by a radical of the formula

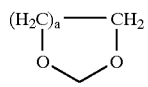

or —$OR^{14}$, in which
a denotes a number 1, 2 or 3 and
$R^{14}$ denotes hydrogen or straight-chain or branched alkyl, hydroxy-substituted alkyl or alkoxycarbonyl each having up to 5 carbon atoms or a radical of the formula —$SiR^{15}R^{16}R^{17}$,
in which
$R^{15}$, $R^{16}$ and $R^{17}$ are identical or different and denote phenyl, straight-chain or branched alkyl having up to 5 carbon atoms, and the heterocyclic and/or benzo-fused ring ($R^1/R^2$) is optionally substituted up to 3 times in an identical or different manner, optionally also geminally, by straight-chain or branched alkoxy or alkoxycarbonyl each having up to 4 carbon atoms, hydroxyl, carboxyl or phenyl, which for its part can be substituted by fluorine, chlorine, bromine, trifluoromethyl or by straight-chain or branched alkyl or alkoxy each having up to 4 carbon atoms, and/or is optionally substituted up to 4 times, optionally also geminally, in an identical or different manner by cyclopropyl, cyclopropyloxy, cyclopentyl, cyclopentyloxy, cyclohexyl, cyclohexyloxy or by straight-chain or branched alkyl having up to 4 carbon atoms, which for its part can be substituted by hydroxyl, trifluoromethyl, phenyl or by straight-chain or branched alkoxy having up to 3 carbon atoms and/or is optionally substituted by a spiro-linked radical of the formula

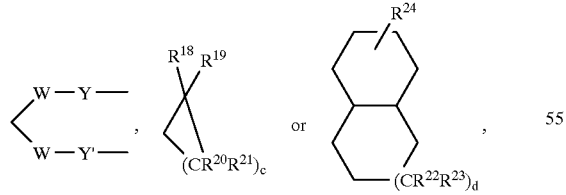

in which
W denotes either an oxygen or a sulphur atom,
Y and Y' together form a 2- to 5-membered, straight-chain or branched alkylene chain,
c denotes a number 1, 2, 3, 4, 5 or 6,
d denotes a number 1 or 2,
$R^{18}$, $R^{19}$, $R^{20}$, $R^{21}$, $R^{22}$, $R^{23}$ and $R^{24}$ are identical or different and denote hydrogen, trifluoromethyl, phenyl, fluorine, chlorine, bromine or straight-chain or branched alkyl or alkoxy each having up to 5 carbon atoms or $R^{18}$ and $R^{19}$ or $R^{20}$ and $R^{21}$ in each case together form a straight-chain or branched alkylene chain having up to 5 carbon atoms or $R^{18}$ and $R^{19}$ or $R^{20}$ and $R^{21}$ in each case together form a radical of the formula —W—$CH_2$
|
—W—$(CH_2)_e$, in which
W has the meaning indicated above,
e denotes a number 1, 2, 3, 4, 5 or 6, and their salts and N-oxides.

3. Heterocyclic-fused pyridines of the formula according to claim 1
in which
A represents phenyl which is optionally substituted by fluorine, chlorine, bromine, hydroxyl, trifluoromethyl, trifluoromethoxy, nitro or by straight-chain or branched alkyl or alkoxy each having up to 3 carbon atoms,
D represents a radical of the formula
$R^5$—X— or

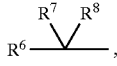

in which
$R^5$ and $R^6$ independently of one another
denote cyclopropyl, naphthyl, phenyl, pyridyl, quinolyl, indolyl, benzothiazolyl or tetrahydronaphthalenyl, each of which is optionally substituted up to 2 times in an identical or different manner by trifluoromethyl, trifluoromethoxy, fluorine, chlorine, bromine, hydroxyl, carboxyl, amino, by straight-chain or branched alkyl, acyl, alkoxy or alkoxycarbonyl each having up to 4 carbon atoms or by phenyl, phenoxy or thiophenyl, which for their part can be substituted by fluorine, chlorine, bromine, trifluoromethyl or trifluoromethoxy,
X denotes straight-chain or branched alkylene or alkenylene having up to 4 carbon atoms, each of which is optionally substituted by hydroxyl,
$R^7$ denotes hydrogen or fluorine and
$R^8$ denotes hydrogen, fluorine, chlorine, bromine, azido, trifluoromethyl, hydroxyl, amino, trifluoromethoxy or methoxy, or
$R^7$ and $R^8$, together with the carbon atom, form a carbonyl group,
E represents cyclopropyl, cyclobutyl, cyclopentyl, cyclohexyl or cycloheptyl, or represents straight-chain or branched alkyl having up to 5 carbon atoms, which is optionally substituted by cyclopentyl or cyclohexyl,
$R^1$ and $R^2$ together form an alkylene chain having up to 4 carbon atoms, which is interrupted by an oxygen or sulphur atom or by the group —$SO_2$— or —$NR^{13}$,
where
$R^{13}$ denotes hydrogen or straight-chain or branched alkyl or acyl each having up to 4 carbon atoms, or denotes benzyl or phenyl, each of which is optionally substituted up to 2 times in an identical or different manner by fluorine, chlorine, bromine, hydroxyl, nitro, trifluoromethyl or straight-chain or branched alkyl or acyl each having up to 3 carbon atoms, and where the heterocyclic ring thus formed, which can also be benzo-fused and which can contain a double bond, must always be substituted by a carbonyl group or by a radical of the formula

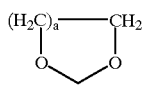

in which
a denotes a number 1, 2 or 3 and
$R^{14}$ denotes hydrogen or straight-chain or branched alkyl hydroxy-substituted alkyl or alkoxycarbonyl each having up to 4 carbon atoms or a radical of the formula $-SiR^{15}R^{16}R^{17}$,
in which
$R^{15}$, $R^{16}$ and $R^{17}$ are identical or different and denote phenyl, straight-chain or branched alkyl having up to 4 carbon atoms, and the heterocyclic and/or benzo-fused ring ($R^1/R^2$) is optionally substituted up to 3 times in an identical or different manner, optionally also geminally, by straight-chain or branched alkoxy or alkoxycarbonyl each having up to 3 carbon atoms, hydroxyl, carboxyl or phenyl which, for its part, can be substituted by fluorine, chlorine, bromine, trifluoromethyl or by straight-chain or branched alkyl having up to 3 carbon atoms, and/or is optionally substituted up to 3 times, optionally also geminally, in an identical or different manner by cyclopropyl, cyclopropyloxy, cyclopentyl, cyclopentyloxy, cyclohexyl or by straight-chain or branched alkyl having up to 3 carbon atoms, which for its part can be substituted by hydroxyl, trifluoromethyl, phenyl or methoxy and/or is optionally substituted by a spiro-linked radical of the formula

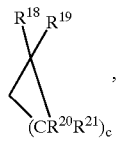

in which
c denotes a number 1, 2, 3, 4 or 5,
$R^{18}$, $R^{19}$, $R^{20}$ and $R^{21}$ are identical or different and denote hydrogen, trifluoromethyl, phenyl, fluorine, chlorine, bromine or straight-chain or branched alkyl or alkoxy each having up to 4 carbon atoms or
$R^{18}$ and $R^{19}$ or $R^{20}$ and $R^{21}$ in each case together form a straight-chain or branched alkylene chain having up to 4 carbon atoms or $R^{18}$ and $R^{19}$ or $R^{20}$ and $R^{21}$ in each case together form a radical of the formula

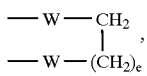

in which
W denotes either an oxygen or sulphur atom and
e denotes a number 1, 2, 3, 4 or 5, and their salts and N-oxides.

4. Heterocyclic-fused pyridines of the formula according to claim 1
in which
A represents phenyl which is optionally substituted by fluorine, chlorine or bromine and
E represents cyclopentyl/isopropyl.

5. Heterocyclic-fused pyridines according to claim 1 as medicaments.

6. Process for the preparation of heterocyclic-fused pyridines according to claim 1 characterized in that in the compounds of the general formula (II)

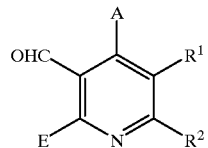

(II)

in which
A, E, $R^1$ and $R^2$ have the meaning indicated above,
first, with organometallic reagents, the substituent D is introduced in inert solvents according to a Grignard or Wittig reaction,
and if appropriate the substituents mentioned under A, E and/or $R^1$ and $R^2$ are varied or introduced according to customary methods.

7. Medicaments comprising at least one heterocyclic-fused pyridine according to claim 1, and a physiologically acceptable formulation auxiliary.

8. Medicaments according to claim 7 for the treatment of arteriosclerosis.

9. A pharmaceutical composition useful for the treatment of dislipidaemia, hyperlipoproteinaemia, hypertriglyceridaemia, hyperlipidaemia or arteriosclerosis comprising an amount effective therefor of a compound according to claim 1 and a pharmaceutically acceptable formulation auxiliary.

10. A method of treating dyslipidaemia, hyperlipoproteinaemia, hypertriglyceridaemia, hyperlipidaemia or arteriosclerosis comprising administering to a patient in need of such treatment an effective amount of a compound according to claim 1.

* * * * *